US008247229B2

(12) United States Patent
Odorico et al.

(10) Patent No.: US 8,247,229 B2
(45) Date of Patent: Aug. 21, 2012

(54) METHOD OF DIFFERENTIATING STEM CELLS INTO CELLS OF THE ENDODERM AND PANCREATIC LINEAGE

(75) Inventors: Jon Odorico, Fitchburg, WI (US); Xiaofang Xu, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 56 days.

(21) Appl. No.: 12/825,281

(22) Filed: Jun. 28, 2010

(65) Prior Publication Data

US 2011/0081720 A1 Apr. 7, 2011

Related U.S. Application Data

(62) Division of application No. 11/799,659, filed on May 2, 2007, now abandoned.

(60) Provisional application No. 60/796,662, filed on May 2, 2006.

(51) Int. Cl.
*C12N 5/00* (2006.01)
(52) U.S. Cl. ......... 435/377; 435/325; 435/366; 435/375
(58) Field of Classification Search .................. None
See application file for complete search history.

(56) References Cited

U.S. PATENT DOCUMENTS

| | | | |
|---|---|---|---|
| 7,033,831 B2 * | 4/2006 | Fisk et al. ...................... | 435/377 |
| 7,045,353 B2 * | 5/2006 | Benvenisty ................... | 435/377 |
| 7,148,062 B2 | 12/2006 | Xu et al. | |
| 7,510,876 B2 | 3/2009 | D'Amour et al. | |
| 7,534,608 B2 | 5/2009 | Martinson et al. | |
| 7,541,185 B2 * | 6/2009 | D'Amour et al. ............. | 435/377 |
| 7,585,672 B2 * | 9/2009 | Odorico et al. ............... | 435/366 |
| 7,985,585 B2 * | 7/2011 | D'Amour et al. ............. | 435/366 |
| 2007/0254359 A1 | 11/2007 | Rezania et al. | |

FOREIGN PATENT DOCUMENTS

WO  2006001699 A1  2/2006

OTHER PUBLICATIONS

Mizusawa, et al., Differentiation phenotypes of pancreatic islet R>- and a-cells are closely related with homeotic genes and a group of differentially expressed genes, Gene 331, Elsevier B.V. (2004) 53-63.

Marchetti, et al., The pancreatic beta-cell in human Type 2 diabetes, Nutrition Metabolism & Cardiovascular Diseases (2006) 16, S3-S6.
Suarez-Pinzon, et al., Combination Therapy with Epidermal Growth Factor and Gastrin Induces Neogenesis of 2 Human Islet β-Cells from Pancreatic Duct Cells and an Increase in Functional 13-Cell Mass, The Journal of Clinical Endocrinology & Metabolism (2005) 90(6): 3401-3409.
Substantive Office Action, dated Mar. 2, 2009, pp. 1-6; European Patent Application No. 07776639.
International Search Report dated Oct. 9, 2007, pp. 1-5; International Patent Application No. PCT/US2007/01062.
Substantive Office Action May 7, 2009, pp. 1-6; Swedish patent Application No. 0850111-6.
Brolen, G.K.C., et aL, "Signals From the Embryonic Mouse Pancreas Induce Differentiation of Human Embryonic Stem Cells" Diabetes 54:2867-2874 (2005).
D'Amour, K.A., et aL, "Efficient differentiation of human embryonic stem cells to definitive endoderm," Nature Biotechnology 23:1534-1541 (2005).
Kahan, B.W., et aL, "Pancreatic Precursors and Differentiated Islet cell types From Murine Embryonic Stem Cells," Diabetes 52:2016-2024 (2003).
Kuso, A., et aL, "Development of definitive endoderm from embryonic stem cells in culture." Development and Disease Research Article 131 :1651-1662 (2004).
Moritoh, Y., et aL, "Analysis of Insulin-Producing Cells During In Vitro Differntiation From Feeder-Free Embryonic Stem Cells." Diabetes 52: 1163-1168 (2003).
Phillips., B.W., et aL, "Directed Differentiation of Human Embryonic Stem Cells into the Pancreatic Endocrine Lineage," Stem Cells and Development 16:561-578 (2007).
Schuldiner, M.• et aL, "Effects of eight growth factors on the differntiation of cells derived from human embryonic stem cells," PNAS 97:11307-11312 (2000).
Segev, H., et aL, "Differentiation of Human Embryonic Stem Cells into Insluin-Producing Clusters," Stem Cells 22:265-274 (2004).
Ying, Q., et al. BMP Induction of Id Proteins Suppresses Differentiation and Sustains Embryonic Stem Cell Self-Renewal in Collaboration with STAT3, Cell, 2003, 115(3): 281-292.
Varge, A.C., et al., The Disparate Role of BMP in Stem Cell Biology, Oncogene, 2005, 24: 5713-5721.

* cited by examiner

*Primary Examiner* — Q. Janice Li
(74) *Attorney, Agent, or Firm* — Quarles & Brady, LLP

(57) ABSTRACT

Methods are described to more efficiently produce cells of the endoderm and pancreatic lineage from mammalian pluripotent stem cells. These methods provide a simple, reproducible culture protocol using defined media components to enable consistent, large-scale production of pancreatic cell types for research or therapeutic uses.

23 Claims, 17 Drawing Sheets

Generation of pancreatic lineage cells from human ES cells

Stage 1: (4 days)
Initiation of hESC differentiation in mesendoderm direction
Treatment of hESCs with 50ng/ml BMP4 on gelatin-coated tissue culture surface with irradiated MEF as feeder cells
(or on Matrigel with 50ng/ml BMP4 and 100ng/ml bFGF)

↓

Stage 2: (14 days)
Production and Proliferation of PDX1 + cells
Generation of EBs from small ESC colonies «70 J..lm) in MEF conditioned medium. Addition of 100 *ng/ml* bFGF during this stage further promotes pdx1 + cell production

↓

Stage 3: (variable periods of time)
Terminal differentiation of pancreatic lineage cells; Formation of Insulin+/C-peptide+/PDX1 + cell clusters
plating of EBs on gelatin-coated tissue culture surface in serum free ITSFNE
media (insulin-transferrin-selenium-FGF7-nicotinamide-exendin-4)

FIG. 1 a
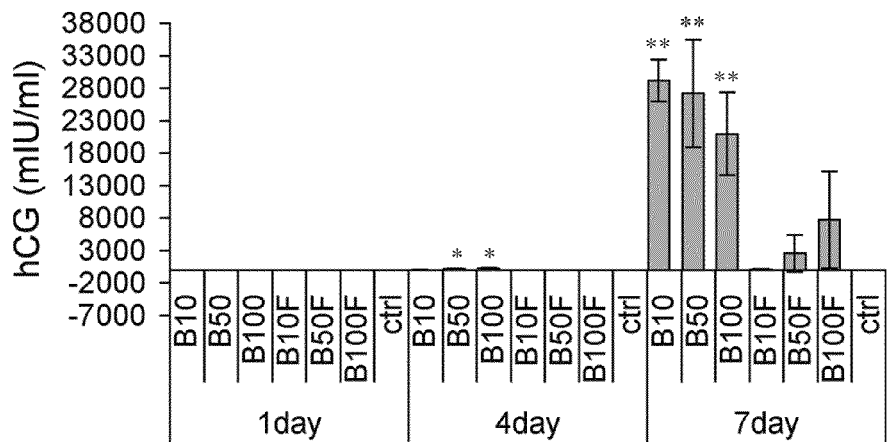
b
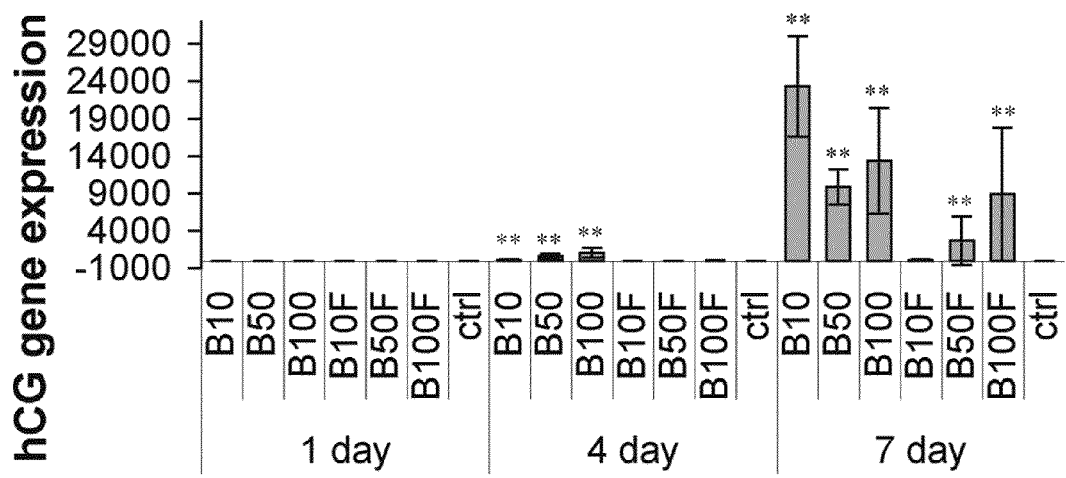
FIG. 2a-b

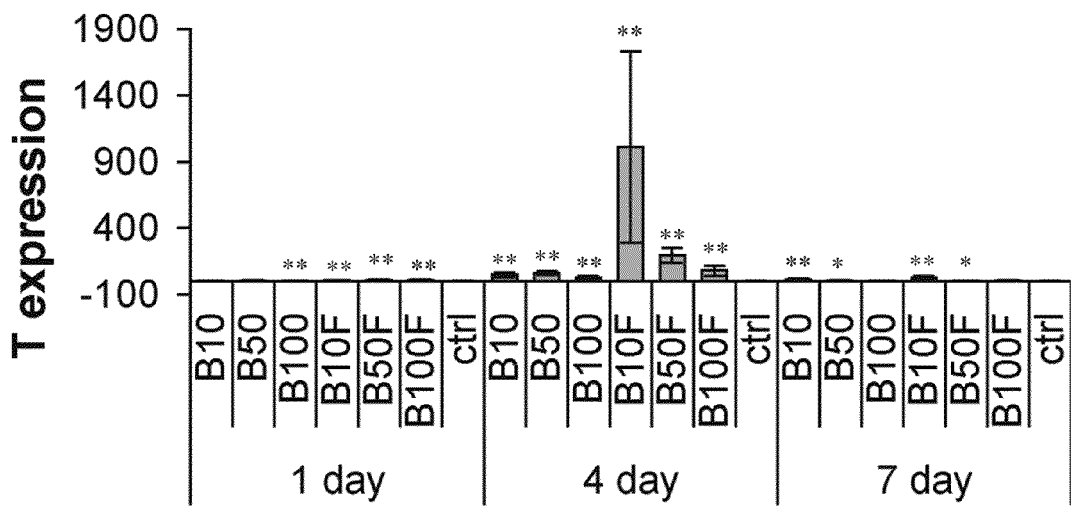
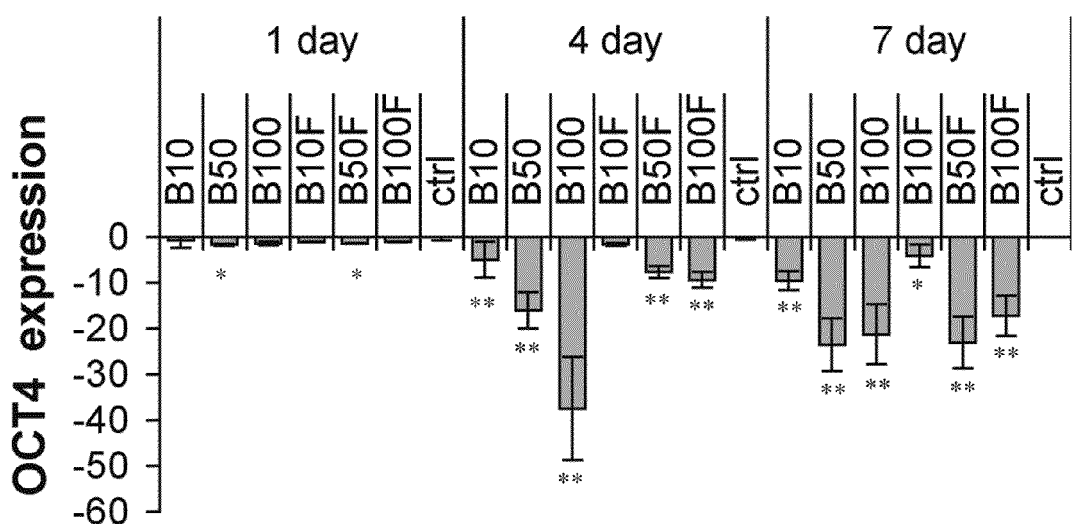
FIG. 2c-d

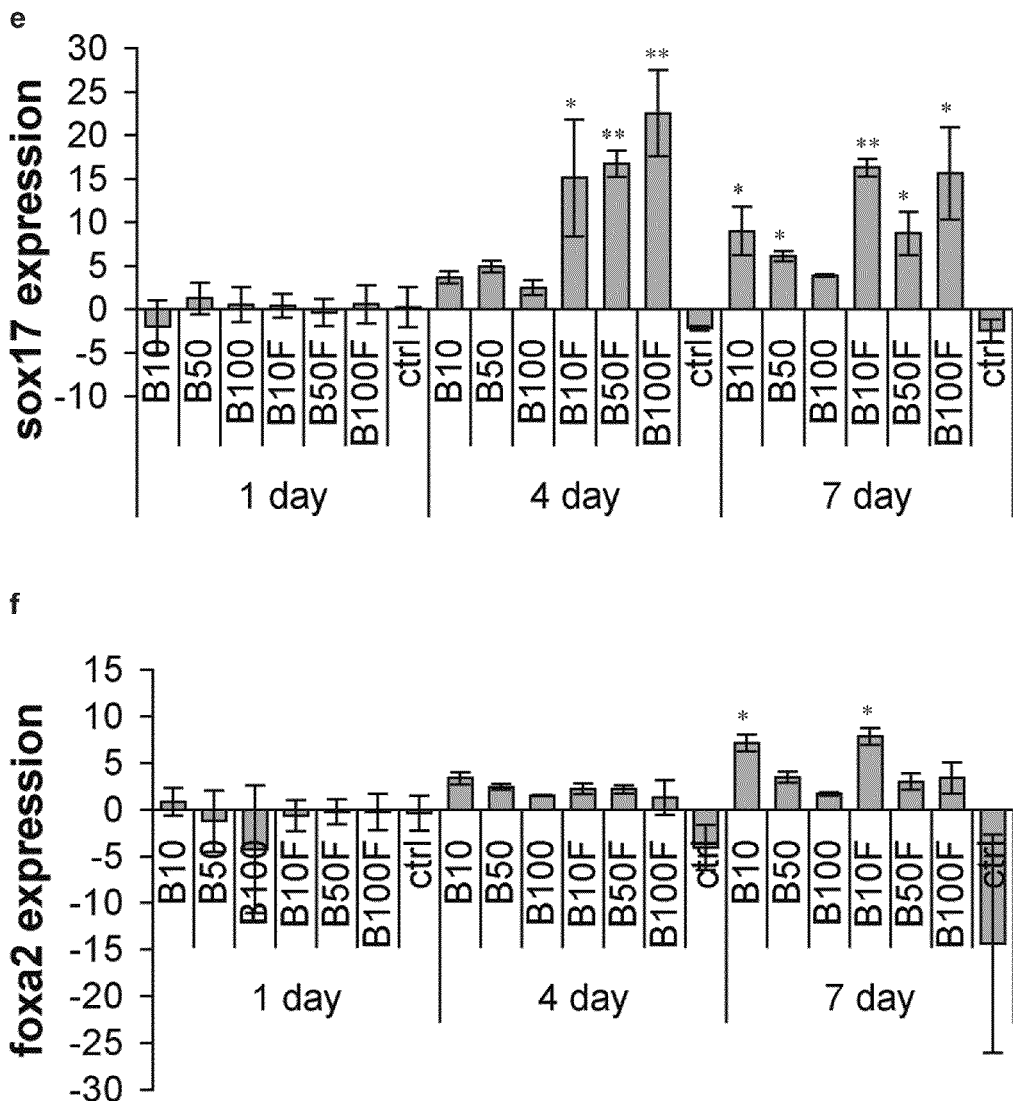
FIG. 2 e-f

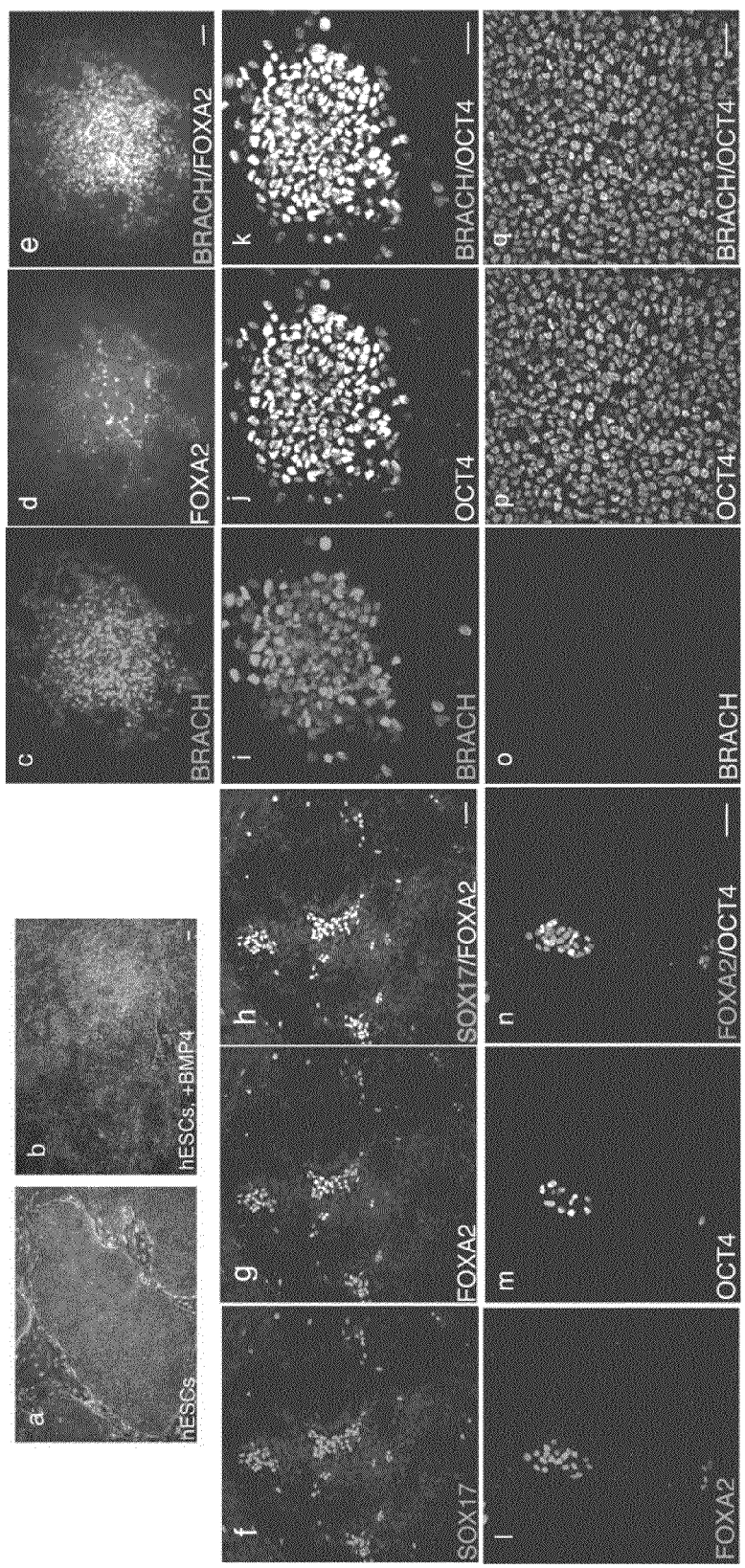
FIG. 3 a-q

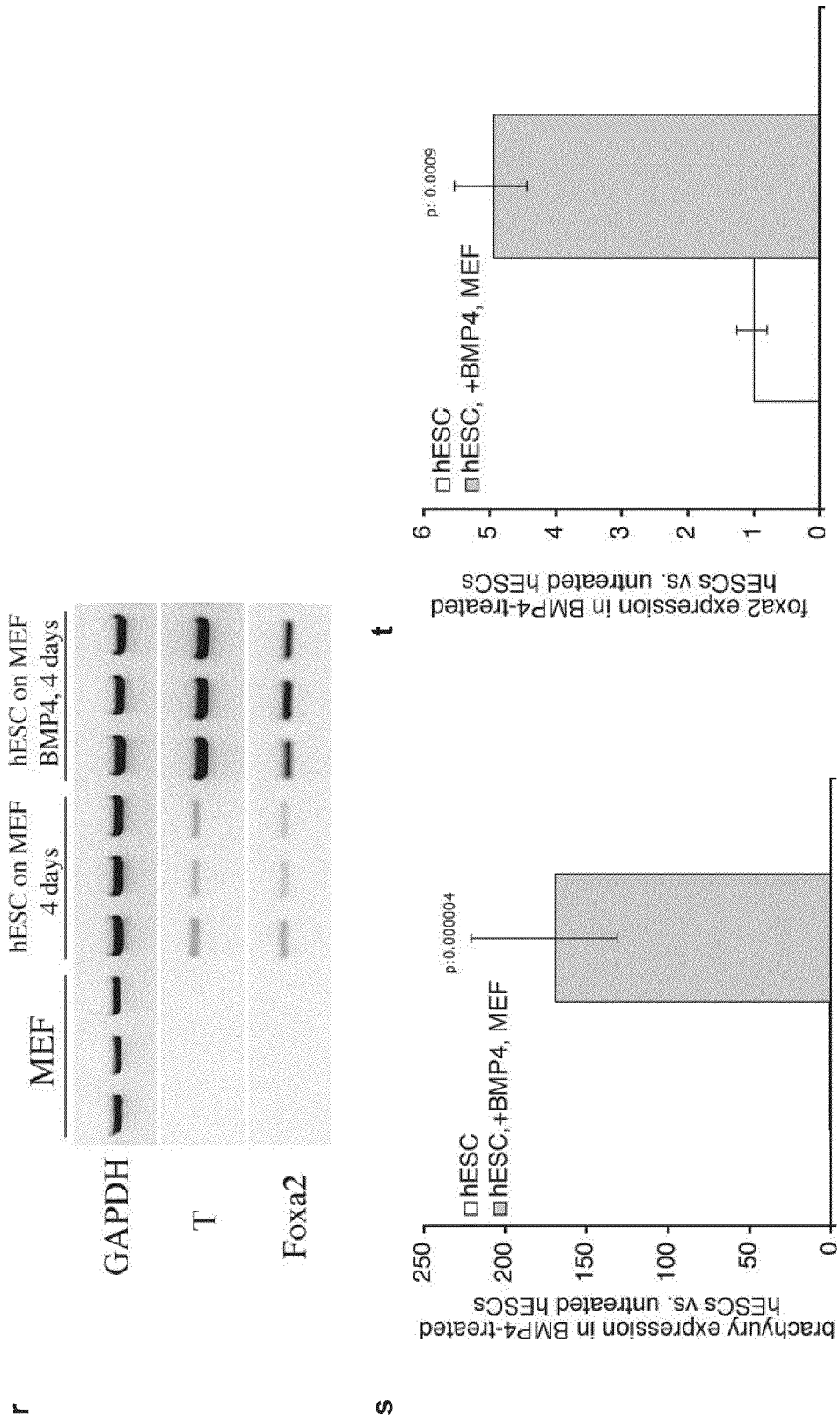
FIG. 3r-t

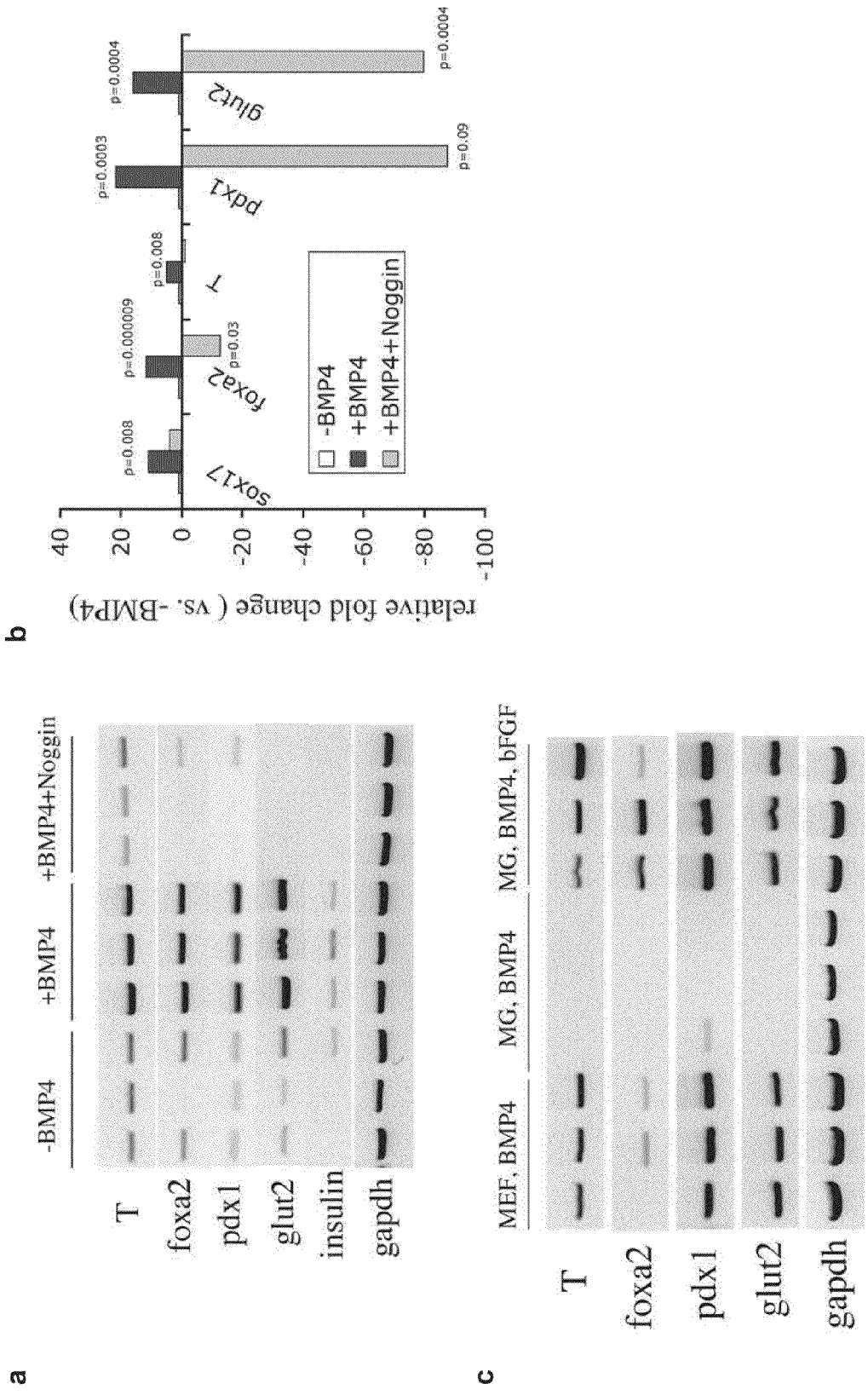
FIG. 4a-c

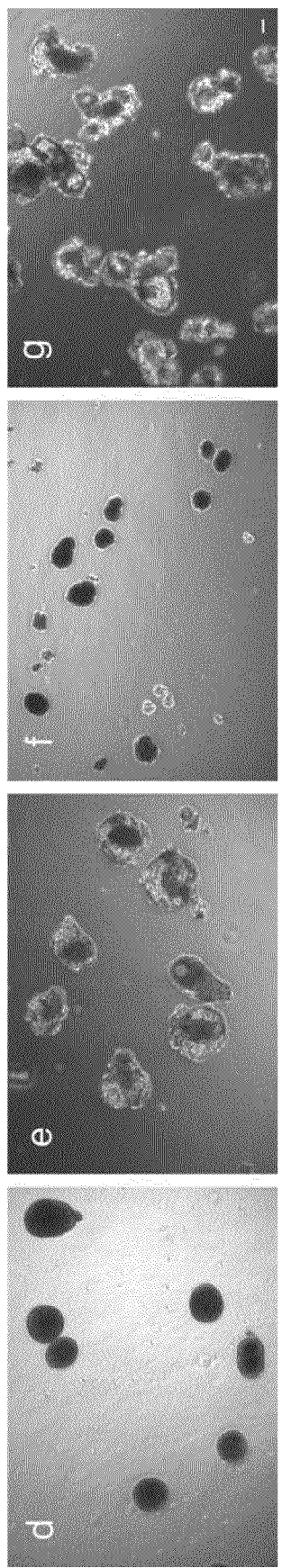
FIG. 4 d-g

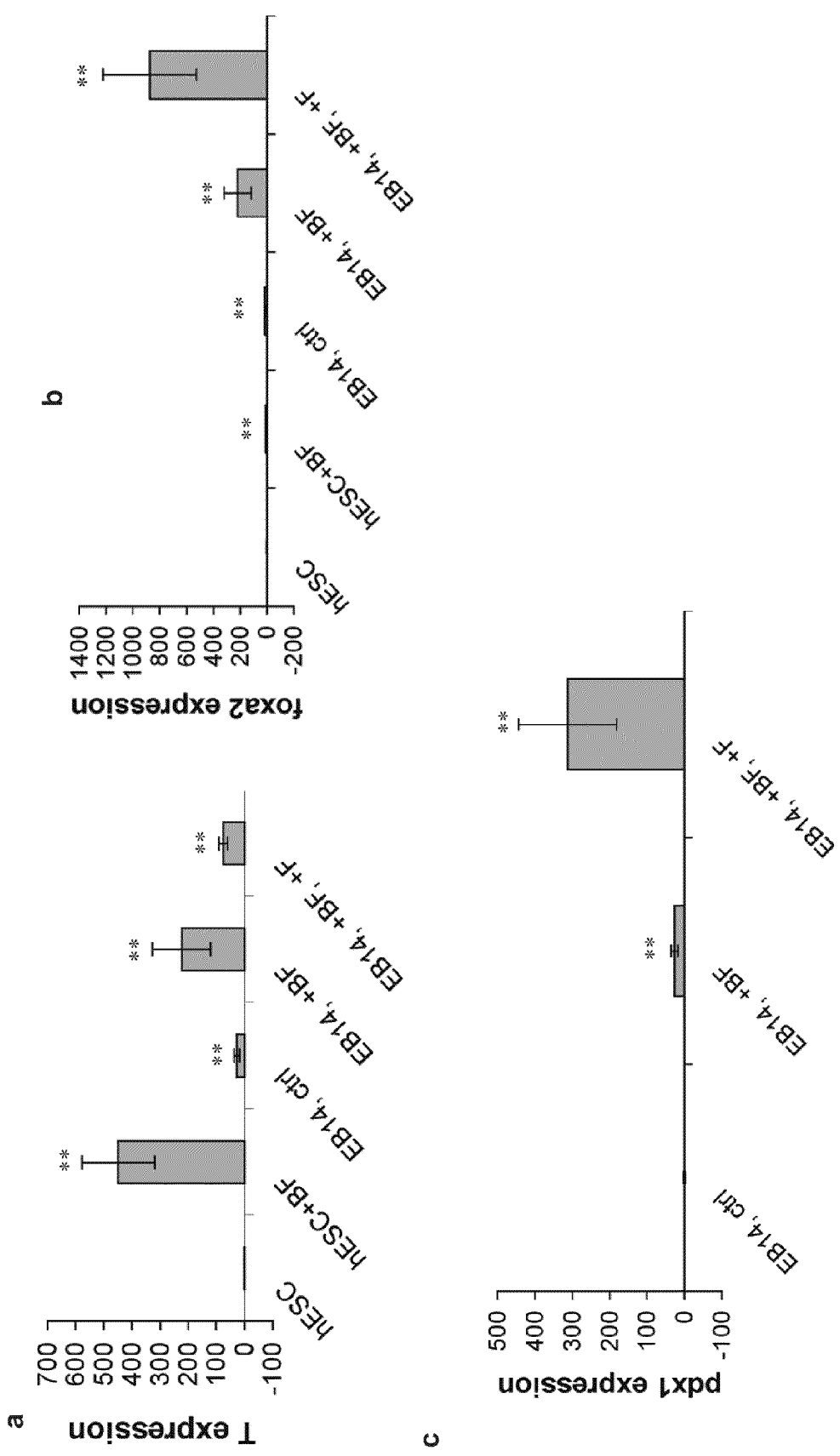
FIG. 5 a -c

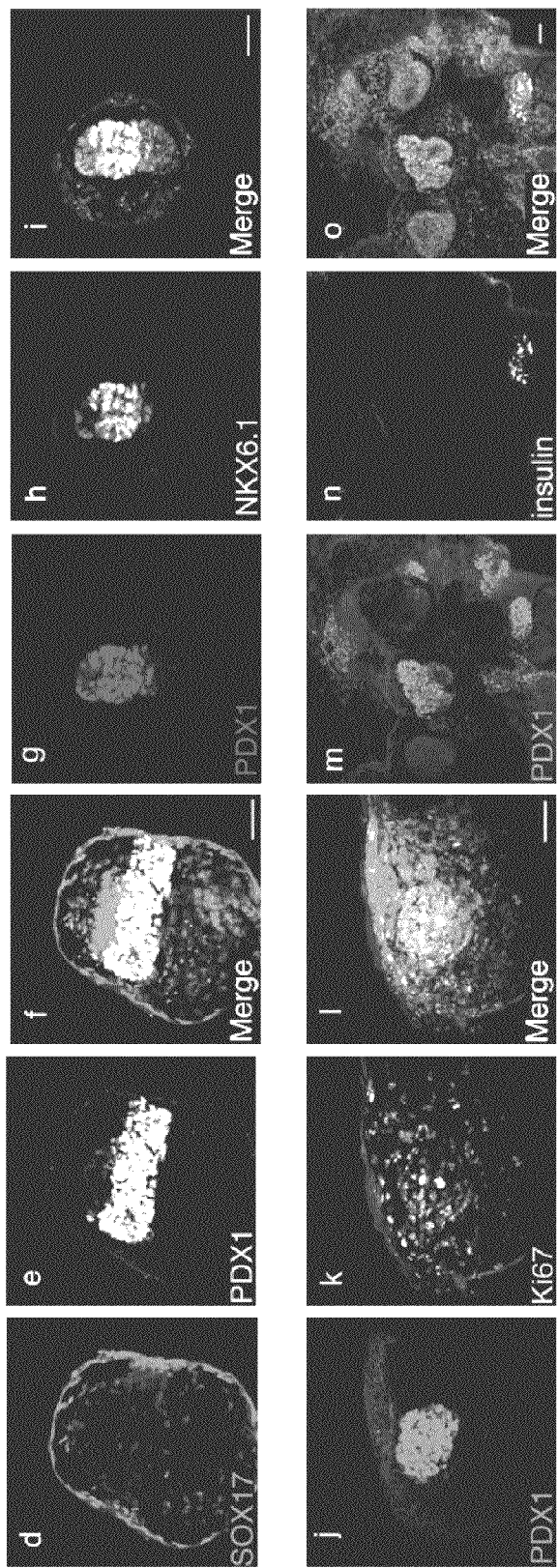
FIG. 5 d-o

Assay numbers from Applied Biosystems for Q-PCR

| Gene | Forward Primer |
|---|---|
| foxa2 | Hs00232764_m1, |
| sox17 | Hs00751752_s1, |
| brachyury | Hs00610080_m1, |
| ngn3 | Hs00360700_g1, |
| pdx1 | Hs00426216_m1, |
| insulin | Hs00356618_m1, |
| glucagon | Hs00174967_m1, |
| glut2 | Hs00165775_m1 |
| β-actin | Hs99999903_m1, |

FIG. 11

| Gene | Forward Primer | SEQ ID NO | Reverse Primer | SEQ ID NO | Amplicon size (base pairs) | Cycle Number |
|---|---|---|---|---|---|---|
| pdx1 | GGATGAAGTCTACCAAAGCTCACGC | 1 | CCAGATCTTGATGTGTCTCTCGGTC | 2 | 230 | 40 |
| oct4 | GGGGTTCTATTTGGGAAGGTATTC | 3 | ATTCTCCAGGTTGCCTCTCACATC | 4 | 228 | 25 |
| foxa2 | GGGAGCGGTGAAGATGGAAG | 5 | TCAGGCTGGGACTCAAGTGC | 6 | 326 | 35 |
| brachyury | AAGAACGGCAGGAGGATGTTTC | 7 | CCCAACTCTCACTATGTGGATTCG | 8 | 333 | 35 |
| sox17 | GGGATACGCCAGTGACGACC | 9 | GCTCTGCCTCCTCCACGAAG | 10 | 350 | 35 |
| ngn3 | GTAGAAAGGATGACGCCTCAAACC | 11 | GCTGCTTGCTCAGTGCCAAC | 12 | 250 | 35 |
| nkx6.1 | ACACGAGACCCACTTTTTCCG | 13 | TGCTGGACTTGTGCTTCTTCAAC | 14 | 336 | 35 |
| nkx2.2 | TTCTACGACAGCAGCGACAACC | 15 | CGTCACCTCCATACCTTTCTCG | 16 | 393 | 40 |
| glut2 | ATGCTCTGGTCCCTGTCTGTATCC | 17 | TGACTAATAAGAATGCCCGTGACG | 18 | 350 | 35 |
| insulin | CAGCCTTTGTGAACCAACAC | 19 | GCTTTATTCCATCTCTCTCGG | 20 | 327 | 40 |
| glucagon | TCAGATGAACGAGGACAAGCG | 21 | CCTGGCGGCAAGATTATCAAG | 22 | 361 | 35 |
| GAPDH | CGGATTTGGTCGTATTGGGC | 23 | CAGGGGATGATGTTCTGGAGAGC | 24 | 559 | 25 |

FIG. 12

METHOD OF DIFFERENTIATING STEM CELLS INTO CELLS OF THE ENDODERM AND PANCREATIC LINEAGE

CROSS-REFERENCE TO RELATED APPLICATIONS

This application is a divisional of U.S. Nonprovisional application Ser. No. 11/799,659 filed May 2, 2007, now abandoned, which claims priority to U.S. Provisional Application No. 60/796,662 filed May 2, 2006. Each of these applications is incorporated by reference here in its entirety.

STATEMENT REGARDING FEDERALLY SPONSORED RESEARCH OR DEVELOPMENT

This invention was made with government support under DK042502 awarded by the National Institutes of Health. The government has certain rights in the invention.

BACKGROUND OF THE INVENTION

Type I diabetes is an autoimmune disease of humans caused by destruction of pancreatic islet beta cells. At present the disease is irreversible, although its symptoms are controlled by the administration of exogenous insulin. Type I diabetes is one of the most common autoimmune diseases in human populations and is a major public health concern.

It has previously been found that transplantation of a whole pancreas or of isolated islet cells is an effective treatment for Type I diabetes to restore insulin independence, when combined with immunosuppressive therapy. The success of existing therapies with isolated islets from human cadaver donors is a proof in principle that a cell-based therapy for human diabetes can be successful. However, the lack of available organs or islet cells has restricted this therapy only to very selected patients. The amount of islet cells which can be harvested from human cadavers is extremely limited. Therefore, a technology that is capable of producing significant quantities of islet cells would be highly desirable with regard to potential therapies for this disease.

Primate and human embryonic stem cells (ESCs) have been isolated and proliferated in culture. Embryonic stem cells are stem cells that can be maintained indefinitely through self-renewal and proliferation in culture, but which also retain the ability to differentiate spontaneously into cells of many different lineages. Under nonselective conditions, it has been previously demonstrated that a wide variety of stem cells, including mouse and human ESCs, will differentiate spontaneously into cells of many lineages including the pancreatic lineage. It has been previously shown that such differentiated cells can express the pancreatic duodenal homeobox 1 (PDX 1) gene, a transcription factor specifying the pancreatic lineage and can also express the insulin hormone. However, without selective conditions, stem cells will spontaneously differentiate into a wide variety of different lineages and only a small proportion of the cells will be differentiated towards any particular lineage.

Culture systems that allow the spontaneous differentiation of hESCs into insulin-staining cells have been reported (Assady, S. et al., Insulin production by human embryonic stem cells. *Diabetes* 50, 1691-1697 (2001); and Segev, H. et al., Differentiation of human embryonic stem cells into insulin-producing clusters. *Stem Cells* 22, 265-274 (2004)). However, these studies neither investigated endoderm marker expression nor demonstrated development of cells possessing stereotypical characteristics of β cells: simultaneous expression of C-peptide and pancreatic duodenal homeobox 1 (PDX1), which is required for pancreas formation and co-activates the insulin promoter (Jonsson, J. et al., Insulin-promoter-factor 1 is required for pancreas development in mice. *Nature* 371, 606-609 (1994)). Because non-β cells such as neuronal cells, may express insulin (Sipione, S. et al., Insulin expressing cells from differentiated embryonic stem cells are not beta cells. *Diabetologia* 47, 499-508 (2004)), and insulin present in the culture media may be taken up into other cell types under certain conditions in vitro (Rajagopal, J. et al., Insulin staining of ES cell progeny from insulin uptake. *Science* 299, 363 (2003)), it is important that the endoderm and pancreatic origin of insulin-staining cells derived from hESCs be ascertained.

It was recently reported that spontaneous differentiation of human ESCs produced PDX1+/FOXA2+ cells and co-transplantation of these differentiated cells with mouse dorsal pancreas (E13.5) resulted in PDX1+/insulin+ cells, and co-staining of insulin and C-peptide was observed (Brolen, G. K. et al., Signals from the embryonic mouse pancreas induce differentiation of human embryonic stem cells into insulin-producing beta-cell-like cells. *Diabetes* 54, 2867-2874 (2005)). This report demonstrated that pancreatic lineage cells can be induced from spontaneously-differentiating human ESCs by signals emanating from the embryonic pancreas. However, the experimental methods would be impractical to adopt into a high-throughput culture protocol and the nature of the molecular signals was not revealed by this study. In addition, unselected stem cell populations are tumorigenic, meaning that they will generate non-malignant tumors, known as teratomas, in immunodeficient animals in the same way that undifferentiated ES cells will.

Several studies have evaluated the effects of growth factors on human ESC differentiation to endoderm (Schuldiner, M. et al., Effects of eight growth factors on the differentiation of cells derived from human embryonic stem cells. *Proc Natl Acad Sci USA* 97, 11307-11312 (2000) and D'Amour, K. A. et al. Efficient differentiation of human embryonic stem cells to definitive endoderm. *Nat. Biotechnol.* 23, 1534-1541 (2005). Yet, the state of the art is that reproducible, highly efficient differentiation to pancreatic precursors and islet cells is not routinely achievable. Furthermore, insulin producing cells generated using previously reported methods are less responsive to glucose (i.e. less functionally mature) than adult human beta cells and are believed to possess a phenotype more like immature beta cells. Taken together, these studies indicate that additional signals may be necessary to convert endoderm into pancreatic progenitors and insulin expressing cells into maturely functional beta cells. Studies of growth factor regulation of pancreas development in embryo models may provide important insights for directing hESC differentiation towards the pancreatic lineage (Wells, J. M. & Melton, D. A. Early mouse endoderm is patterned by soluble factors from adjacent germ layers. *Development* 127, 1563-1572 (2000)). For example, in a chick-quail chimera system, it was demonstrated that BMP4 induces pdx1 expression in uncommitted endoderm and noggin blocks pdx1 expression in committed endoderm (Kumar, M. et al., Signals from lateral plate mesoderm instruct endoderm toward a pancreatic fate. *Dev. Biol.* 259, 109-122 (2003)).

Methods have been discussed in the patent literature for the differentiation of human ESCs, or other human pluripotent cell types, into pancreatic or pancreatic islet cells. However, as the technology of stem cell culture moves ahead, improvements in the techniques to culture various differentiated cell types are critical to the ultimate commercial use of these differentiated cells. The previous techniques reported for culturing human ESCs into cells of the pancreatic lineage, while suitable for laboratory scale investigations, can not be readily scaled up to reliably and consistently produce large numbers of pancreatic cell types for research or for therapeutic uses. Thus, a simple, reproducible culture method utilizing defined components that promotes islet differentiation from human pluripotent stem cells is a desirable addition to the field.

BRIEF SUMMARY OF THE INVENTION

The present invention is broadly summarized as novel methods for direct in vitro differentiation of human pluripotent stem cells to cells of the endoderm and pancreatic lineage. The method involves culturing the stem cells with an effective amount of a bone morphogenetic protein to induce differentiation in the direction of mesendoderm. These mesendoderm cells are further cultured to form embryoid bodies (EBs), which under defined conditions terminally differentiate to cells of to the pancreatic lineage. By utilizing defined components that promote pancreatic islet differentiation from human pluripotent stem cells, the methods of the invention provide a simple, reproducible culture protocol enabling large-scale production of pancreatic cell types for research or for therapeutic uses.

In a related aspect, the method includes culturing human pluripotent stem cells in an effective amount of a bone morphogenetic protein and a fibroblast growth factor to induce differentiation in the direction of mesendoderm. This initial culture step is followed by further culturing the cells under defined conditions to induce differentiation of pancreatic lineage cells.

Another feature of the direct differentiation methods described herein is the ability to isolate on a large scale endoderm and pancreatic cells, such as beta cells.

The methods described herein also overcome one of the largest hurdles to potential use of stem cell derived cells for transplant, the tumorigenic character of undifferentiated stem cells. These methods may be used for deriving populations of pancreatic islet cells that do not form teratomas when transplanted into hosts.

In one aspect, isolated cell populations derived from human pluripotent stem cells that have committed to the mesendoderm and endoderm lineages are disclosed. The cells of this lineage are characterized by their ability to differentiate further into pancreatic islet cells, suitably beta cells. In a related aspect, at least 50% of the terminally differentiated cells of the pancreatic lineage are characterized by their ability to simultaneously express at least one or more of insulin, c-peptide, and PDX1 markers.

Unless otherwise defined, all technical and scientific terms used herein have the same meaning as commonly understood by one of ordinary skill in the art to which this invention belongs. Although suitable methods and materials for the practice or testing of the present invention are described below, other methods and materials similar or equivalent to those described herein, which are well known in the art, can also be used.

Other object features and advantages of the present invention will become apparent from the following specification.

BRIEF DESCRIPTION OF THE SEVERAL VIEWS OF THE DRAWINGS

FIG. 1 is a flowchart summarizing the general method of preparing pancreatic lineage cells from human ES cells.

FIG. 2, comprising FIGS. 2(a-f), shows a time-course of the expression of genes: (a) secreted hCG protein levels from cultures of BMP4/bFGF-treated hESCs; (b) human chorionic gonadotropin (hCG), (c) brachyury (T), (d) oct4, (e) sox17 and (f) foxa2.

FIG. 3, comprising FIGS. 3(a-t), shows that BMP4 initiated mesendoderm differentiation characterized by expression of Brachyury, Foxa2 and Sox17. FIGS. 3 (a-n) are photomicrographs of BMP4-treated hESCs and FIGS. 3 (o-q) are photomicrographs of untreated hESCs: (a) Homogeneous colonies of hESC grown on MEF for 4 days. (b) hESCs grown on MEF and treated with 50 ng/ml BMP4 for 4 days become heterogeneous and display an altered cellular morphology (Stage 1). (c-e) BMP4-treated hESCs display clusters of brachyury-(BRACH) positive cells intermingled with FOXA2-positive cells. (f-h) FOXA2 cells co-stain with SOX17. (i-k) In BRACH-positive cell clusters in BMP4-treated hESCs, many cells are co-stained with OCT4. (l-n) No co-staining of FOXA2 and OCT4 is observed. (o-q) Untreated hESCs are stained with OCT4, but not with BRACH. FIGS. 3 (r-t): RT-PCR (r) and Q-PCR (s, t) indicate changes in mRNA levels of brachyury (T) and Foxa2. Scale bar for (a-b), 100 μm; for (c-q): 50 μm.

FIG. 4, comprising FIGS. 4 (a-g), shows the effects of BMP4 and bFGF treatment of hESCs on endoderm- and pancreas-associated gene expression and on EB morphology. FIGS. 4 (a) RT-PCR and (b) Q-PCR analysis depicts changes in expression of endoderm-(sox17, foxa2, pdx1) and pancreas-associated (pdx1, glut2, insulin) genes at EB14 for hESCs either untreated, treated with 50 ng/ml BMP4, or treated with both 50 ng/ml BMP4 and 300 ng/ml Noggin. FIG. 4 (c) depict mRNA levels from either hESCs grown on MEF treated with 50 ng/ml BMP4 or hESCs grown on Matrigel™ treated with 50 ng/ml BMP4 alone, or treated with both 50 ng/ml BMP4 and 100 ng/ml bFGF and analyzed at the EB14 stage. FIGS. 4 (d-g) are representative phase contrast images of 14 day EB suspension cultures from untreated or treated hESCs as follows: (d) EBs from untreated hESCs grown on MEF; (e) EBs from BMP4-treated hESCs grown on MEF; (f) EBs from BMP4-treated hESCs grown on Matrigel™; (g) EBs from hESCs grown on Matrigel™ treated with both BMP4 and bFGF. Scale bar, 100 μm.

FIG. 5, comprising FIGS. 5 (a-o), characterize EBs or Stage 2 cells. FIGS. 5 (a-c) are graphs showing expression levels of endoderm and pancreas associated genes in hESC-derived EB14s. FIGS. 5 (d-o) show immunostaining of EB14s, where bFGF was added during the EB stage and more than 50% of cells are stained with PDX1.

FIGS. 7 (a-c) show that EBs plated in ITSFNE media for 14 days show co-staining of PDX1 and insulin. FIGS. 7 (d-f) depict most PDX1-positive cells no longer co-stain with KI67 at this stage. FIGS. 7 (g-i) show that larger clusters of PDX1+ insulin+ co-staining cells appearing by EB14+28. FIGS. 7 (j-l) show that no PDX1 or insulin staining is observed in cultures previously not treated with BMP4. FIGS. 7 (*m-p*) show that cells co-stained with Insulin, C-peptide and PDX1 at EB14+28. This pattern is indicative of normal beta cells. Scale bar, 50 μm.

FIGS. 8 (*a-d*) show that glucagon-positive cells are not co-stained with C-peptide and PDX1, as would be expected on normal adult alpha cells. FIGS. 8 (*e-h*) show that somatostatin-positive cells are not co-stained with C-peptide, but some appear to co-stain with PDX1 as would be expected on normal adult delta cells. Scale bar, 50 μm.

FIG. 11 is a table showing a list of Applied Biosystems TaqMan Assays used for quantitative and non-quantitative PCR analysis of gene expression.

FIG. 12 is a table listing primer sequences used for quantitative and non-quantitative PCR analysis of gene expression.

DETAILED DESCRIPTION OF THE INVENTION

Figure 6:
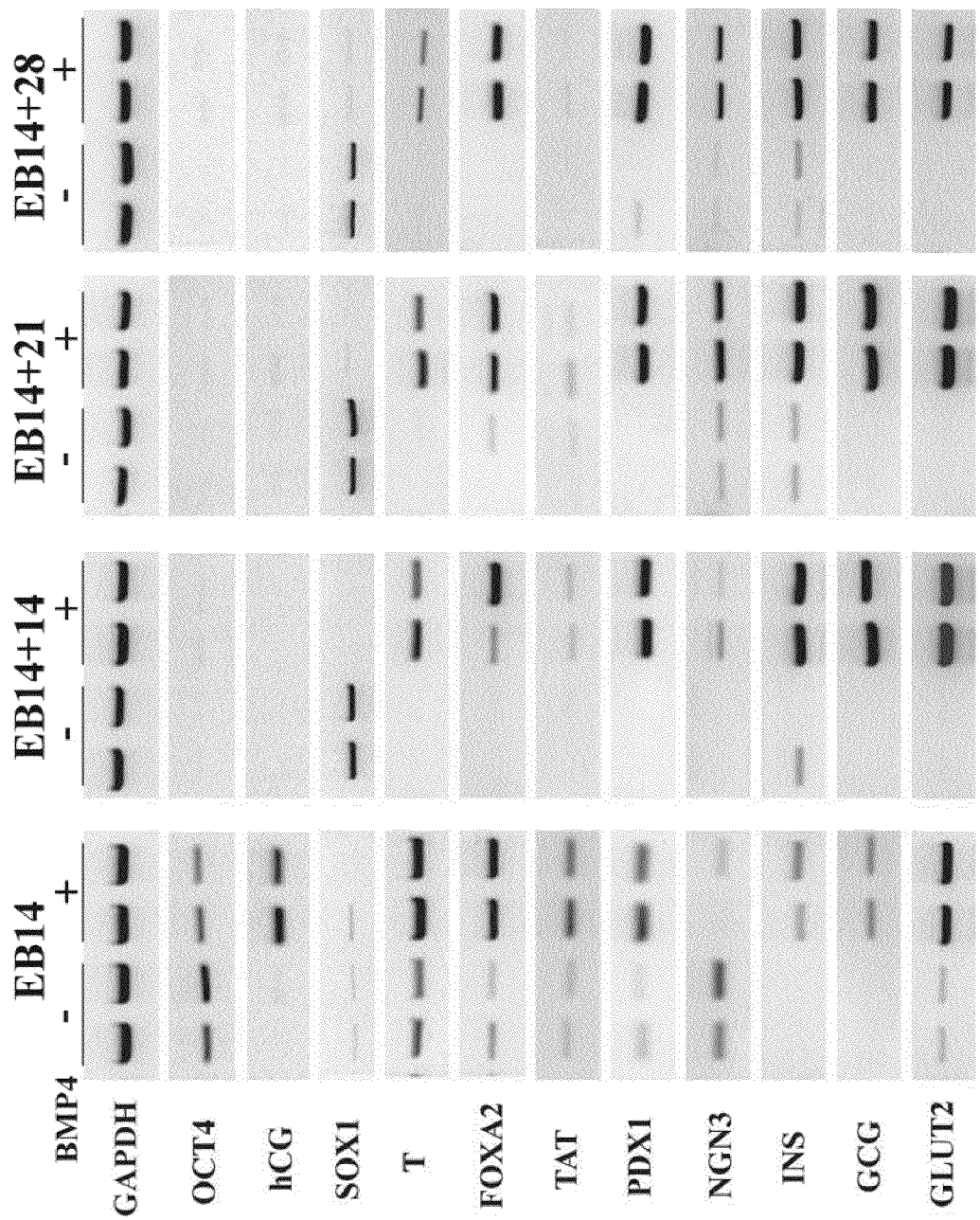
FIG. 6 depicts a time-course of gene expression after plating intact EBs and culturing for 14, 21, and 28 days in growth factor-supplemented serum-free ITSFNE media (Stage 3). EBs were from untreated (−) or BMP4-treated (+) hESCs grown on MEF. The expression of genes marking early neural (sox1), mesendoderm (T), undifferentiated ESCs (oct4), trophoblasts (human chorionic gonadotrophin, hCG), definitive endoderm (foxa2, pdx1), liver (tyrosine amino transferase, TAT), and islet endocrine cell types (ngn3, insulin, glucagon, glut2) were analyzed by RT-PCR.

The present invention broadly relates to novel methods for direct in vitro differentiation of mammalian pluripotent stem cells to cells of the pancreatic lineage. The methods involve culturing the stem cells in the presence of an effective amount of a bone morphogenetic protein to induce differentiation in the direction of mesendoderm. These mesendoderm cells are further cultured to form embryoid bodies (EBs) enriched for definitive endoderm committed cells, which under defined conditions terminally differentiate to cells of the pancreatic lineage. By utilizing defined media components that promote pancreatic islet differentiation, the described methods provide a simple, reproducible approach to enable large-scale production of pancreatic cell types for research or therapeutic uses.

In an effort to better understand the methods disclosed herein and the scientific literature surrounding them, it is noted that recent studies with human embryonic stem cells (hESCs) have begun to focus on the differentiation of definitive endoderm as a first step toward development of pancreatic lineage cells. Others have reported on Activin A induction of definitive endoderm from hESCs (see D'Amour, K. A., et al. (2005)). However, pancreatic lineage cells were not induced by this protocol. Furthermore, preliminary results testing Activin A (at 5 ng/ml, 50 ng/ml, or 100 ng/ml) in serum-free media suggest that this treatment alone cannot induce pancreatic cell differentiation. This is not surprising given that it has been demonstrated that, in the absence of feeder cells, Activin A can maintain pluripotency of hESCs (Beattie, G. M. et al., Activin A maintains pluripotency of human embryonic stem cells in the absence of feeder layers. *Stem Cells* 23, 489-495 (2005)). Other hESC studies evaluating pancreatic differentiation have either been inconclusive as to the origin of insulin staining cells or required a period of in vivo growth in undefined conditions (Brolen, G. K. et al., (2005)).

With the goal of identifying culture conditions that promote efficient derivation of β cells from hESCs, a series of pilot experiments were conducted to test a number of growth factors, cytokines and developmentally-relevant molecules, including FGF4 (10 or 50 ng/ml), retinoic acid ($10^{-9}$M), FGF10 (10 ng/ml), activin A (5 ng/ml, 50 ng/ml or 100 ng/ml), cyclopiamine (1 μM or 10 μM) and BMP4 (5 ng/ml, 50 ng/ml or 100 ng/ml) at different stages of hESC differentiation. Of the factors tested, BMP4 treatment of hESCs grown on MEFs had by far the strongest enhancing effect on pdx1 expression.

The intercellular signaling molecule BMP4 is known to play an important role in fate determination and lineage development during embryogenesis. Several studies in other vertebrates have shown that BMP4 inhibits early neurogenesis in ESC cultures and promotes pancreatic endoderm specification from uncommitted endoderm (Kumar, et al., Signals from lateral plate mesoderm instruct endoderm toward a pancreatic fate. *Dev. Biol.* 259, 109-122 (2003) and Finley, et al., BMP-4 inhibits neural differentiation of murine embryonic stem cells. *J. Neurobiol.* 40, 271-287 (1999)). Based on these studies applicants hypothesized that BMP4 might enhance endoderm and pancreatic differentiation from hESCs.

Again, through experimentation, applicants have shown that BMP4 treatment of hESCs promotes mesendoderm differentiation and subsequently supports pancreatic differentiation. Applicants' data, together with the data of Xu, et al., were used to identify a dosage effect of BMP4 on hESCs. It was found that treatment with 100 ng/ml alone transforms nearly all hESCs into trophoblast cells, whereas lower doses were able to guide differentiation of hESCs to mesendoderm and definitive endoderm.

It is known that certain inductive events in vivo mediated by mesoderm-derived embryonic tissues (i.e. notochord, dorsal aortae, lateral plate mesoderm) play an important role in the patterning of uncommitted foregut endoderm and the specification of a pancreatic fate (Wells, J. M. & Melton, D. A. (2000); and Kumar, et al. (2003)). Applicants believe that effects from other cell types and germ layers may be necessary for the further maturation of endoderm cells and production of PDX1+ cells from hESCs. The production of pancreatic cell types from ESCs is probably a multi-step process, likely involving the sequential steps of definitive endoderm induction, endoderm patterning and induction of pancreas epithelium, each of which requires proper environmental cues, such as soluble growth factors and cytokines, and perhaps direct contact with other cell types.

Others report that PDX1+/FoxA2+ cells were produced when hESCs have direct contact with MEFs and insulin-producing cells were produced from PDX1+/FoxA2+ cells after in vivo exposure to murine dorsal pancreas signals (Brolen, et al., (2005)). On the other hand, it was recently reported that highly purified murine definitive endodermal cells failed to express pancreatic markers after short-term culture (Tada, S. et al., Characterization of mesendoderm: a diverging point of the definitive endoderm and mesoderm in embryonic stem cell differentiation culture. *Development* 132, 4363-4374 (2005)). Similarly, purified cultures of Activin A-induced hESC-derived endodermal cells were not shown to express pdx1 and other signals may be necessary (see D'Amour, et al., (2005)).

By contrast, applicants discovered that use of an intermediate level of BMP4 results in adoption of a mesendoderm fate (brachyury+) by many cells. The endoderm marker FoxA2 arises during the initial treatment of hESCs with BMP4 and MEF or with BMP4 and bFGF. Further, FoxA2 expression gradually increases throughout the entire differentiation process and is associated with duct-like structures in EBs. Subsequent pdx1 gene expression and the emergence of PDX1+ cells also occurred during the EB phase. Although FoxA2 expression is not unique to definitive endoderm, the (1) proximity of the cells to brachyury+ cells, (2) observed co-staining with Sox17, (3) absence of neural markers, such as sox1, (4) low abundance of trophoblast markers in these EBs, and (5) simultaneous expression of PDX1 suggest that the FoxA2+ cells are likely to represent pre-pancreatic endoderm or endoderm-derived cell populations. These results suggest that by employing a multi-step procedure involving early BMP4 and bFGF induction of mesendoderm with defined culture conditions illustrated in FIG. 1, definitive endoderm and pancreatic lineage cells may be sequentially derived from hESCs.

Accordingly, in a broad embodiment of the invention, the method provides a method of culturing human pluripotent stem cells in a medium containing an effective amount of bone morphogenetic protein to induce differentiation into a mesendoderm direction. As used herein, mammalian pluripotent stem cells include primate and preferably human embryonic stem cells (hESCs) described by Thomson et al. (*Science* 282:1145, 1998). These cells are characterized as being capable under appropriate conditions of producing several different cell types that are derivatives of all of the three germinal layers (endoderm, mesoderm, and ectoderm). According to a standard art-accepted test, these pluripotent cells also have the ability to form a teratoma in 8-12 week old SCID mice.

In some aspects of this embodiment, the pluripotent stem cells are cultured on a gelatin-coated tissue culture surface with irradiated mouse embryonic fibroblast (MEF) as feeder cells. Feeder cells are cells of one type that are co-cultured with cells of another type, to provide an environment in which the cells of the second type can grow. The length of culture time for this step ranges from about 1 day to about 10 days, preferably 4 days. Inducers of the bone morphogenetic signaling pathway include but are not limited to bone morphogenetic proteins (BMPs), suitably BMP2 and BMP7 and most suitably, BMP4.

As used herein, an effective amount of a BMP encompasses a concentration ranging from about 10 ng/ml to about 100 ng/ml. It is noted that while larger dosages of BMP4 have been shown to induce human pluripotent stem cell differentiation into trophectoderm lineages, it is disclosed here that culturing stem cell colonies with low to intermediate amounts of BMP4, suitably 50 ng/ml, works synergistically with MEFs or high concentrations of bFGF, such as 100 ng/ml, promoting the differentiation of the stem cells in the mesendoderm direction.

As used herein, mesendoderm cells are defined by and are not limited to the expression of Brachyury and Oct 4 nuclear transcription factor markers (see Stage 1 in FIG. 1). Mesendoderm cells may also be characterized by expression of Wnt3 and FGF4 (D'Amour et al. 2005) and/or goosecoid (Gsc), Ecadherin, Mixl1, and FoxA2, and possibly Sox17 (Yasunaga et al. Nat. Biotechnol. 2005).

In the second phase of this embodiment, the cultures are induced to form embryoid bodies (EBs) from small pluripotent stem cell colonies in MEF conditioned media. Suitably, the EBs are intact and are surrounded by a layer of visceral yolk sac (VYS), which express stage specific embryonic antigen-3 (SSEA-3). The length of culture time for this step ranges from about 1 day to about 4 weeks, preferably 14 days. As used herein, EBs are three dimensional structures of groups of cells which interact in such a way to induce further differentiation within the cells of the EB (see Stage 2 in FIG. 1). Suitable EBs include definitive endoderm cells with duct-like structures, which include cells expressing Foxa2, Sox17 and PDX1. It is believed that these endoderm cells give rise to cells of the pancreatic lineage. As used herein, pancreatic lineage cells include, for example, cells co-expressing PDX1 and Nkx6.1, which are well known to represent either pancreatic epithelial progenitor cells or beta cells. These cells are the only two cell types in the body expressing this combination of markers or PDX1, insulin, and C-peptide, which are well known to be simultaneously expressed in normal beta cells; or cells expressing somatostatin generally understood to represent delta cells.

Cells within EBs derived from BMP4 treated hESCs were characterized by immunostaining and Quantitative PCR as containing a significant subset co-expressing both PDX1 and Nkx6.1 markers (see FIG. 4). Some of the cells also appear to express the Ki67 marker indicating they are proliferating. Another subset appears to be capable of committing to a terminally differentiated endocrine lineage.

In the third phase of this embodiment, the cells from the EBs are plated onto tissue culture plates in a serum-free medium (without fetal bovine serum (FBS)) intended to induce terminal differentiation into cells of the endocrine lineage. In this step, the length of time the cells are cultured for varies from about 7 day to about 56 days, suitably 28 days. Suitable terminally differentiated cells are characterized by the simultaneous expression of insulin, C-peptide and PDX1. Other cell types of the endocrine lineage, such as glucagon-expressing cells and somatostatin-expressing cells also appear in this context and in these regions of the cultures. A significant proportion of PDX1+ cells at these stages (stage 2 and stage 3) are found to co-express the cell surface marker epithelial cell adhesion molecule (EpCAM)

As used herein, serum-free medium means serum-free DMEM/F12 (17.5 mM glucose) medium with ITS supplement (BD, 5 µg/ml insulin+5 µg/ml transferrin+5 ng/ml selenous acid), 10 ng/ml FGF7 (R&D), 10 mM nicotinamide (Sigma), 10 nM exendin-4 (Sigma), and 2 g/L BSA (Sigma). Hence, the serum-free medium is termed ITSFNE for insulin-transferrin-selenium-FGF7-nicotiamide-exendin 4 (see Stage 3 in FIG. 1). A suitable concentration for extendin-4 ranges from about 0.1 mM to about 1 mM. Also, the concentration of nicotinamide may range from about 1 to about 25 mM.

Alternatively, in a related and more suitable embodiment, the human pluripotent stem cells may be initially cultured without feeder cells, suitably on Matrigel™. When culturing hESCs on Matrigel, applicants discovered that in addition to inducers of the bone morphogenetic pathway, an effective amount of fibroblast growth factors (FGFs) was required to induce the cells to differentiate in the mesendoderm direction. The concentration of FGF ranges from about 10 to about 200 ng/ml. A suitable bFGF concentration is 100 ng/ml. At this stage applicants also discovered that MEFs and the factors they elaborate or produce may replace the function of FGFs in this induction protocol. Supplementing bFGF to the cultures at Stage 2 leads to significantly more cells of endoderm and pancreatic lineages, which express the appropriate markers. The medium may be supplemented with other suitable fibroblast growth factors, such as FGF2. To characterize the cells of these three developmental stages, an RNA expression time-course for a variety of endoderm- and pancreas-associated genes was performed and described below.

In some embodiments, the invention is also directed toward methods for deriving pancreatic cell enriched populations of cells, suitably beta cells that do not form teratomas when transplanted into hosts. Accordingly, it is contemplated that the stage 3 cells of pancreatic lineage can be rendered non-tumorigenic by sorting cells on the basis of cell surface markers as described in U.S. Published Application No: 20050260749 to the applicants. Specifically, the differentiated cells are sorted based on the positive expression of the epithelial cell adhesion molecule (EpCAM), a cell surface marker the expression of which can be used for positive selection to identify human cells committed to the endodermal, pancreatic or foregut lineages. For performing this selection, any instrument capable of sorting single cells such as a fluorescence-activated cell sorter (FACS) or magnetic activated cell sorting (MACS) should be adaptable for use in this kind of cell sorting procedure. Using this EpCAM/MACS selection protocol to remove undifferentiated cells remaining in the later stage culture, but also using antibodies to cell surface markers of undifferentiated stem cells such as SSEA3 or SSEA4, applicants discovered that the tumorigenic tendency of stem cell cultures can be reduced effectively.

It is clearly evident from the stem cell literature that when injected into immunocompromised mice, undifferentiated ES cells will form teratomas, which are non-malignant growths or tumors made up of many different tissue types in a poorly organized structure. While the generation of teratomas is not thought to be life-threatening to the host, the teratomas can grow to large size, be unsightly and wasteful of metabolic energy to the host. A characterization of the teratomas formed by human ES cells is found in Gertow et al., *Stem Cells and Development*, 13:421-435 (2004). If human ES cells are to be used ultimately for transplantation of cells or tissues into human patients, the cells which are so introduced would presumably be preferred to be free of tumorigenic capacity. In the art, the main techniques which have been taught to eliminate this capability are based on inserting exogenous gene constructs into ES cells and then selecting for differentiated cells based on expression characteristics of the introduced genes. However, the use of exogenous genes inserted into human ES cell cultures carries another set of safety concerns that are best avoided.

By combining cell surface sorting technology with the direct differentiation methods described herein, applicants reasonably expect at a practical level to produce a stem cell derived cell culture that is not tumorigenic and does not form teratomas. At the risk of redundancy, and to avoid misunderstanding, the use of the phrase tumorigenic is intended to apply to the teratoma-forming characteristics of undifferentiated human undifferentiated stem cells, such as ES cells and is not intended to imply malignancy of any kind. This is because ES cells do not produce frank malignancies when injected into mice. The removal of the tumorigenic trait simply by direct differentiation and selection is another important step in the progression of stem cell derivative from laboratory model to useful human therapy.

In another embodiment, the invention provides an isolated cell population derived from human pluripotent stem cells having terminally differentiated cells of the pancreatic lineage. At least 50% of this cell population simultaneously express one or more of insulin, C-peptide and PDX1.

In still another embodiment, the invention provides an isolated non-tumorigenic cell population derived from human pluripotent stem cells. This cell population has terminally differentiated cells of the pancreatic lineage, wherein at least 70% of the cells simultaneously express one or more of insulin, C-peptide, PDX1, NKX6.1 and EpCAM, and wherein the cells do not form teratomas when injected in immunocompromised mice. Since these cells, suitably Beta cells, develop from cultures that harbor cells having a phenotype of endoderm (FoxA2 and Sox17) and pancreatic progenitors (PDX1+, NKX6.1+, and insulin-proliferative), it is expected that they express other markers, such as, NKX2.2, NeurOD, Pax4 and IS11.

The following examples are provided as further non-limiting illustrations of particular embodiments of the invention.

EXAMPLES

Example 1

Cell Culture and Differentiation

The general differentiation method is illustrated in simplistic fashion in FIG. 1. NIH approved hESC lines, H1 (WA01) and H9 (WA09) were used between passage 24 to 40. Media for undifferentiated ESCs was comprised of 80% DMEM/F12 and 20% Knockout serum replacement supplemented with 1 mM L-glutamine, 1% nonessential amino acids, 0.1 mM 2-mercaptoethanol and 4 ng/ml bFGF (all from Invitrogen). hESCs were cultured in 6-well plates on a feeder layer of irradiated mouse embryonic fibroblasts (MEFs) in either ESC media (control group), ESC media plus 50 ng/ml BMP4 (BMP4 group; R&D systems), or ESC media plus 50 ng/ml BMP4 plus 300 ng/ml noggin (noggin group; R&D systems) for 4 days.

In experiments with Matrigel™, hESCs were grown on growth-factor depleted Matrigel™ (BD Biosciences) instead of MEF and culture media was MEF-conditioned media (CM, control group), CM plus 50 ng/ml BMP4 or CM plus 50 ng/ml BMP4 plus 100 ng/ml bFGF. Colonies were transferred by incubating with 2 mg/ml dispase (Invitrogen), after which cells were rinsed off the plates, pipetted into small pieces, and filtered through a 70 µm cell strainer. The filtrates that contained small pieces of colonies were put into 100-mm non-treated suspension culture dishes with CM on a shaker for 14 days to form embryoid bodies (EBs). EBs were then replated in serum-free DMEM/F-12 (17.5 mM glucose) medium with ITS supplement (BD, 5 µg/ml insulin+5 µg/ml transferrin+5 ng/ml selenous acid), 10 mM nicotinamide (Sigma), 10 ng/ml FGF7 (R&D), 10 nM exendin-4 (Sigma), and 2 g/L BSA (Sigma) for 14, 21 or 28 days, then harvested. A fraction of each culture was used for RT-PCR and Q-PCR and the remaining cells were either embedded in OCT (EB14; Tissue-Tek) or fixed on coverslips (EB14+14, EB14+21 and EB14+28) for immunostaining.

Example 2

Quantitative PCR and RT-PCR

Total cellular RNA was extracted with TriZol (Invitrogen). cDNA was synthesized from 1 µg total RNA using a SuperScript First-Strand Synthesis kit (Invitrogen). Quantitative real time RT-PCR (Q-PCR) was performed using Assays-on-demand agents (Applied Biosystems) on an ABI PRISM 7700 Sequence Detection System (Applied Biosystems) for the following transcripts: foxa2, sox17, brachyury, ngn3, pdx1, insulin, glucagon, glut2 and an endogenous control, β-actin. Q-PCR was performed according to equipment manufacturer's instructions. Relative quantification was carried out using the comparative cycle threshold ($C_T$) methods recommended by the supplier. Fold change was calculated as: $2^{-\Delta\Delta CT}$. Mean $\Delta\Delta C_T$ values from Q-PCR analyses were compared using the unpaired, two-tailed Student's t-test. P values <0.05 were considered significant.

For non-quantitative RT-PCR, oligonucleotide primer pairs were generated against human transcripts using Genebank sequences (see FIG. 12). Primers were selected from two different exons and spanned at least one intronic sequence. PCR was performed using HotStarTaq DNA polymerase (Qiagen) and reaction conditions were as follows: initial denaturation at 95° C. for 15 min, then cycles of 94° C. for 30 sec, 30 sec at annealing temperature, 1 min at 72° C., and a final 10 min at 72° C. Primers were annealed at 53° C. except for pdx1 (56° C.), sox17 (55° C.) and foxa2 (50° C.; with Qiagen's Q-solution). A control sample without reverse transcriptase (−RT) was amplified with GAPDH primers in all cases, and human adult pancreas RNA was used as a positive control.

Example 3

Immunofluorescence Staining

Immunofluorescence staining of coverslips was carried out as previously described (Kahan, B. W. et al., Pancreatic precursors and differentiated islet cell types from murine embryonic stem cells: an in vitro model to study islet differentiation. *Diabetes* 52, 2016-2024 (2003)). The following primary antibodies were used at the listed dilutions: PDX1 rabbit anti-mouse serum 1:4000 (gift of C. Wright); insulin mouse monoclonal 10 μg/ml (ATCC No: HB124); glucagon mouse monoclonal 1:2000 (Sigma); somatostatin mouse monoclonal 1:2000 (Novonordisk); Ki-67 mouse monoclonal 1:25 (BD Pharmingen); C-peptide rat monoclonal 1:3000 (BCBC 1921); Brachyury goat anti-human 1:20 (R&D); OCT4 goat anti mouse 1:100 (Santa Cruz); Sox17 goat anti-human 1:40 (R&D); FOXA2 rabbit anti-rat1:4000 (Gift of R. Costa). Secondary antibodies (Goat anti-mouse lgG Alexa Fluor 488, 1:2000; Goat anti-rabbit Alexa Fluor 568, 1:4000; Goat anti-rat Alexa Fluor 488, 1:2000; Goat anti-rabbit, Alexa Fluor 647, 1:4000; Goat anti-mouse 568, 1:2000; Donkey anti-goat Alexa Fluor 568, 1:2000; Donkey anti-mouse Alexa Fluor 488, 1:2000) were obtained from Molecular probes (Eugene, Oreg.).

Example 4

Mesendoderm Induction by Treating hESCs with BMP4 on MEFs

The process of hESCs differentiation was initiated by treating hESCs with BMP4 on MEFs, as shown overall in FIG. 1. Notably a prior study showed that treatment of hESCs on Matrigel™ with 100 ng/ml BMP4 for 7 days causes nearly 100% of the cells to differentiate into human chorionic gonadotrophin (hCG)-expressing trophoblast cells (Xu, R. H. et al. BMP4 initiates human embryonic stem cell differentiation to trophoblast. *Nature Biotechnology.* 20, 1261-1264 (2002)).

These results were also reproduced as shown in FIG. 2, where after 7 days treatment with BMP4 100 ng/ml alone on Matrigel, the cell types produced abundantly expressed hCG and secreted hCG protein (FIGS. 2a and b). Specifically, undifferentiated hESCs grown on Matrigel (MG) were divided into 7 groups and treated with: (1) 10 ng/ml BMP4 (B10); (2) 50 ng/ml BMP4 (B50); (3) 100 ng/ml BMP4 (B100); (4) 10 ng/ml BMP4+100 ng/ml bFGF (B10F); (5) 50 ng/ml BMP4+100 ng/ml bFGF (B50F); (6) 100 ng/ml BMP4+100 ng/ml bFGF (B100F); (7) control (ctrl): without any added growth factors—for 1 day, 4 days and 7 days. As indicated above, hCG secretion and gene expression were greatly increased in B100 group (FIG. 2a-b). By day 7, average hCG secretion was 21000 mIU/ml in culture medium and hCG gene expression exhibited a 13000-fold increase over the control group (statistical analysis in FIG. 2 are made with values compared to first day control of the same group). Lower concentration of BMP4 (10 ng/ml, 50 ng/ml) in fact had the same degree of hCG-induction effect. On the other hand, bFGF obviously inhibits the hCG-induction effect of BMP4. For example, the average hCG secretion at day 7 in B10 group was 29000 mIU/ml and in B10F group was 51 mIU/ml (FIG. 2a). At same time, T expression was greatly induced in BMP4/bFGF-treated hESCs in a time-dependent manner (FIG. 2c). The induction peaked at day 4 with B10F group with a 1000-fold increase and B50F about 200-fold increase. Sox17 and foxa2 expressions were also increased in BMP4/bFGF-treated hESCs (FIG. 2e-f). Oct4 expression, on the other hand, was significantly decreased, especially in only BMP4-treated groups at day 4 (FIG. 2d).

Applicants also treated undifferentiated hESCs with 50 ng/ml BMP4 for 4 days in the presence of either MEFs or bFGF (100 ng/ml) This treatment morphologically altered the cells, with untreated cells maintaining a homogeneous appearance, and treated cells becoming heterogeneous and clearly changing their morphology (FIG. 3 a-b). BMP4 treatment results in some cells differentiating to Brachyury+ cells, which are intermingled with relatively fewer FoxA2+ cells in the same cell cluster (FIG. 3c-e). Applicants found an average of 10 such clusters per 15 mm coverslip in BMP4-treated cultures, whereas none were detected in untreated hESCs. Brachyury+ cells are also OCT4+, at least transiently (FIG. 3i-k). In contrast, FoxA2+ cells are not OCT4+ (FIG. 3l-n), and nearly all FoxA2+ cells are co-stained with Sox17 (FIG. 3f-h).

FIG. 2 shows that in contrast to cells treated with BMP4 alone, cells treated with low and intermediate doses of BMP4 (10 ng/ml and 50 ng/ml) for 4 days did not express hCG or produce hCG protein; instead, cells expressed significantly greater amounts of brachyury and sox17 transcripts while expressing significantly lower levels of Oct4 transcripts compared to control cells at the same time point (FIG. 2 c-e).

In cultures not treated with BMP4, cells were OCT4+ but did not express Brachyury (FIG. 3o-q). These OCT4 staining data are in concert with recent reports showing that decreased OCT4 expression induces loss of pluripotency and dedifferentiation to trophectoderm whereas, increased OCT4 levels cause differentiation into primitive endoderm and mesoderm (Niwa, H. et al., Quantitative expression of Oct-3/4 defines differentiation, dedifferentiation or self-renewal of ES cells. *Nat. Genet.* 24, 372-376 (2000)). Transcript levels of Brachyury and Foxa2 are supportive of the staining data. Both non-quantitative (FIG. 3r) and quantitative RT-PCR (FIGS. 3s and t) show an increase in brachyury and Foxa2 transcripts when cultures on MEFs are treated with BMP4. Applicants found an approximately 170-fold increase in brachyury gene expression (FIG. 3s) and a roughly 5-fold increase in foxa2 expression with BMP4 treatment (FIG. 3t). Together these data predict that a sequential series of embryonic stages emerge from hESCs. First, brachyury+, and brachyury and Oct4 co-expressing cells (possibly reflecting a transition state) arise, representing mesendoderm. Then, cells go through another rapid transition within a few days to co-express FoxA2 and Sox17, while losing brachyury expression.

Example 5

Several Additional Essential Components for Early Pancreatic Cell Lineage Differentiation from hESCs in vitro are Identified To further define the culture conditions and media additives that promote development of pancreatic cells from hESCs in vitro, applicants evaluated the requirement for MEFs during the BMP4-treatment period. In BMP4-treated cells grown on Matrigel™ transcripts were not detected for any of the genes examined, including brachyury, foxa2, pdx1 and glut2 (FIG. 4c), whereas they were easily detected in BMP4-treated cells grown in MEFs. In addition, hEBs derived from cells grown on MEFs vs. Matrigel™ were morphologically different (FIG. 4d-g). Cells grown on Matrigel™ resulted in EBs that were smaller, more compact, and more opaque than EBs derived from BMP4-treated cells grown in the presence of MEFs. Thus, MEFs play an important role in pancreatic lineage specification in this protocol.

As a high concentration of bFGF has been recently reported to have a MEF-like effect on the growth of hESCs (Ludwig, T. E., et al., Derivation of human embryonic stem cells in defined conditions. *Nat. Biotechnol.* 24, 185-187 (2006) and Levenstein, M. E., et al., Basic FGF Support of Human Embryonic Stem Cell Self-Renewal. *Stem Cells* (2005)), applicants examined whether bFGF could replace MEFs in the culture protocol. To determine this, 50 ng/ml BMP4 and 100 ng/ml bFGF were added to hESCs grown on Matrigel™ for 4 days; cells were then harvested for gene expression analysis. Compared to untreated hESCs, brachyury gene expression was ~1000 fold greater in BMP4- and bFGF-treated hESCs. EBs derived from BMP4- and bFGF-treated cells showed similar morphologies and comparable levels of brachyury, foxa2, pdx1, and glut2 gene expression to EBs from hESCs grown on MEFs and treated with BMP4 (FIGS. 4c and 4e, 4g), suggesting that bFGF plays an early, essential role in endoderm specification and/or pancreatic lineage cell differentiation.

To determine whether the inductive effect of BMP4 on mesendoderm formation from hESCs was dependent on canonical BMP signaling, applicants tested whether the addition of soluble noggin to the culture medium was able to reverse the effect of BMP4 treatment. Gene expression was examined at EB14 by RT-PCR (FIG. 4a) and Q-PCR (FIG. 4b) after treatment of hESCs for 4 days with either 50 ng/ml BMP4 alone, or BMP4 plus 300 ng/ml noggin. The simultaneous addition of noggin and BMP4 is capable of completely blocking gene expression of brachyury, sox17, foxa2, pdx1 and glut2 in BMP4-treated hESC cultures. The effect of noggin was dose dependent (data not shown). It is notable that transcript levels of foxa2 and glut2 in noggin-treated cells were even lower than non-BMP4 treated cells, suggesting that there exists some minimal BMP4-like effect in hESC media or elaborated from hESCs themselves.

Example 6

Embryoid Body (EB) Suspension Culture of BMP4-Treated hESCs Promotes Endoderm and Pancreatic Lineage Cell Differentiation Based on the defined role of BMP4 in pancreas specification in chicken embryos, applicants aimed to determine whether BMP4 treatment would promote differentiation of mesendoderm and pancreatic cells from hESCs. EBs were therefore formed from either untreated hESCs, or hESCs treated with 50 ng/ml BMP4 for 4 days. Applicants' previous experiments showed that differentiation through an EB stage, in which inductive tissue interactions may occur in three dimensions among the early embryonic germ layers, positively influences development of pancreatic lineage cells, compared to differentiation under two-dimensional conditions (Xu et al., Endoderm and pancreatic lineage differentiation from human embryonic stem cells, *Cloning and Stem Cells*, 8, 96-107, (2006))).

Transcript analysis showed no detectable pdx1 expression in untreated hESCs. After the cells were grown as EBs for 14 days, pdx1 mRNA began to appear in the control group. Compared to the untreated group at EB14, BMP4 treatment induced significant up-regulation of genes including: sox17 (11 fold), foxa2 (12 fold), tat (7 fold), pdx1 (22 fold), brachyury (8 fold) and glut2 (19 fold). Although brachyury induction by BMP4 was still significant when cells were analyzed at EB14 (14 fold), the magnitude of increase was much less than at the ESC stage (170 fold, treated hESCs vs. untreated hESCs). Applicants reproducibly observed the BMP4 effect in numerous (more than 15) independent experiments and with two different hESC lines (H1 and H9).

In this regard, FIGS. 5 (a-c) show expression levels of endoderm and pancreas associated genes in hESC-derived EB14s. FIG. 5 (b-c) show that BMP4/bFGF treatment induces significant expression of endoderm and pancreas-associated genes in hESC-derived EBs after 14 days of growth (EB14+BF vs. EB14, ctrl). Also, the addition of 100 ng/ml bFGF during the EB stage (+F) led to a reduction in brachyury (T) transcripts (a) on one hand and on the other, greatly enhanced foxa2 and pdx1 expression (b and c); b) foxa2 transcript levels increased from 219-fold greater than undifferentiated hESCs (without bFGF during the EB phase) to 873-fold greater than undifferentiated hESCs (with bFGF during the EB stage), and c) pdx1 transcript levels increased from 26-fold vs. undifferentiated hESCs (without bFGF during the EB stage) to 312-fold greater than undifferentiated hESCs (with bFGF during the EB stage). Notably, average delta Ct value of pdx1 from QPCR testing was 7.7, comparable to the pdx1 expression level in human islet preparations (approximately 50% pure).

Furthermore, FIGS. 5 (d-o) show immunostaining of EB14s, where bFGF was added during the EB stage and more than 50% of cells are stained with PDX1. The stainings are very strong and nuclear and cells are often formed in clusters. PDX1+ cells are not co-stained with the SOX17 antibody (FIG. 5d-f), yet some PDX1+ cells are co-stained with the NKX6.1 antibody (FIG. 5g-i). Some of the PDX1+ cells are also Ki67+ (FIG. 5j-i), suggesting the existence of proliferating PDX1+ cells.

The immunostaining of EB14 cells also revealed that hESCs were capable of differentiating into mitotically-active pancreatic progenitor cells, expressing PDX1 and Ki67 (FIG. 5j-1). Many PDX1+ cells were seen in the BMP4-treated group, most of which were also Ki67+, suggesting that these cells were actively proliferating. In addition, a significant proportion of cells expressing PDX1 also co-expressed Nkx6.1 (FIG. 5g-i), but the majority did not express insulin at this stage (FIG. 5m-o). PDX1/insulin co-staining began to appear at EB 14 (FIG. 5m-o). Notably, bFGF during the EB stage appears to promote a transition from brachyury expressing cells to the appearance of pancreas lineage committed cells.

The above-noted constellation of markers suggests the cells represent a pancreatic progenitor stage similar to the proliferating pancreatic epithelium that grows and expands during mid-gestation prior to or around the time of the secondary transition when most beta cells form. Furthermore, numerous FoxA2+ cells were seen in duct-like structures, and some cells were also Ki67+. These structures formed during the EB stage may play an important role in the induction of PDX1+ cells. In contrast, PDX1+ and FoxA2+ cells were not seen at these stages of hESC differentiation without BMP4 treatment (data not shown).

Serum is known to have an inhibitory effect on the differentiation of definitive endoderm from ESCs (D'Amour, K. A., et al. (2005)) and pancreatic lineage cell development (Gao, R., et al., Characterization of endocrine progenitor cells and critical factors for their differentiation in human adult pancreatic cell culture. *Diabetes* 52, 2007-2015 (2003)). Cultures in which EBs are plated in 15% serum-containing media show a gradual reduction in pdx1 expression, as well as the expression of other endoderm and pancreatic lineage associated genes (Xu et al., *Cloning and Stem Cells*, 2006). In contrast, pdx1 transcript levels were maintained and/or increased in growth factor-supplemented serum-free media.

Example 7

Human ESCs Yield Cells with PDX1/INSULIN/C-PEPTIDE Co-Staining

To determine if BMP4-treated hESCs have the ability to become fully differentiated, hormone-containing pancreatic islet cells, applicants plated 14 day EBs onto gelatin-coated coverslips in serum-free ITSFNE media for an additional 14, 21 and 28 days. Transcriptional profiles over this time-course were determined by RT-PCR (FIG. 6) and Q-PCR. After plating (EB14+14, EB14+21 and EB14+28), endoderm and pancreas-associated gene transcripts, including foxa2, pdx1, ngn3, insulin, glucagon and glut2, were highly enriched in the BMP4-treated cells compared to untreated cells. Q-PCR data demonstrated the increasing transcript levels of foxa2 (18, 21 and 37 fold increase over the time-course EB14+14, EB14+21 and EB14+28 respectively, compared to untreated EB14), pdx1 (179, 155 and 541 fold increase) and glut2 (47, 97 and 224 fold increase). Importantly, insulin and glucagon transcripts were undetectable in untreated EB14 cells.

In contrast, in BMP4-treated cultures, insulin and glucagon mRNA levels increased dramatically over time. Q-PCR reaction cycles for insulin mRNA change from 50 (undetectable) in EB14 untreated cells to 28, 27 and 25 cycles in BMP4-treated cells over the post-EB differentiation time-course. For glucagon, the change was from 46 cycles to 22, 21 and 20 cycles; in all experiments, β-actin cycle times were approximately 15 cycles. In contrast to the increasing abundance of islet hormone transcripts, brachyury mRNA continuously decreased over time during these late stages and was not significantly different from the level in EB14 untreated cells. Consistent with prior studies in hESCs, the trophoblast marker hCG was expressed in the BMP4-treated cells at EB14 (Xu, R. H., et al. (2002)), but not in EBs generated from hESCs that had not been treated with BMP4. After EBs were plated in serum-free media, hCG mRNA levels decreased dramatically (FIG. 6).

Also in concert with prior observations in embryos and mESCs, the neuroectoderm marker sox1 was not detected in BMP4-treated cells, whereas it was induced in differentiation cultures that had been initiated with untreated hESC colonies (FIG. 6). These data suggest that: 1) serum-free conditions favor islet hormone cell differentiation over trophoblast differentiation (e.g., retained islet hormone gene expression over time vs. lost hCG gene expression over time under serum-free conditions); 2) neural differentiation is likely inhibited by BMP4 treatment and/or neural precursors are not selected by BMP4 treatment, 3) serum-free conditions prevent Oct4-expressing undifferentiated cells from surviving and/or expanding, and 4) TAT-expressing cells, such as liver cells, are not supported or maintained by these serum-free conditions.

Figure 7:
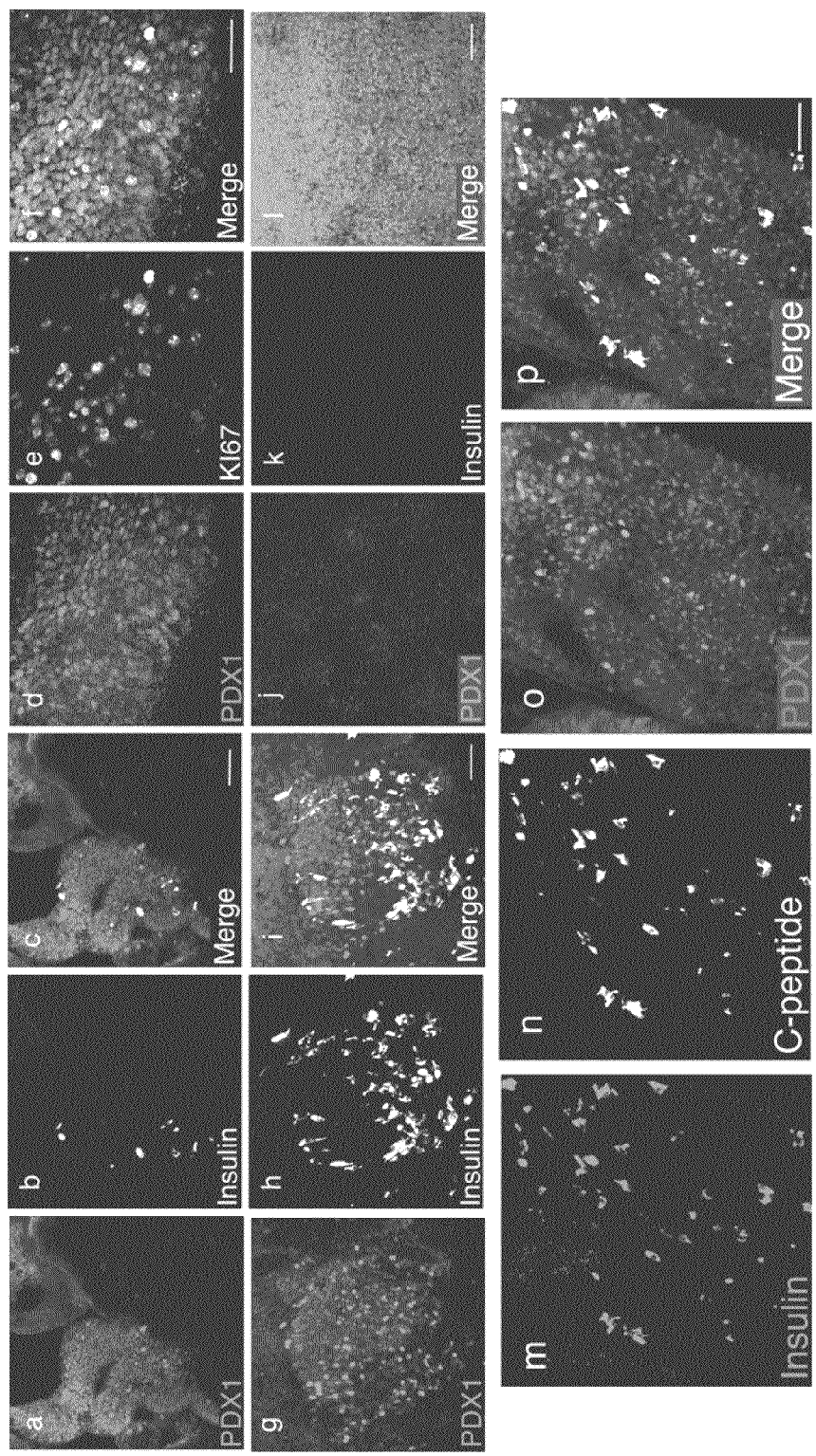
FIG. 7, comprising FIGS. 7 (a-p), are photomicrographs showing that PDX1+/insulin+ cells are present in cultures at Stage 3, viz. a viz., following BMP4 treatment of undifferentiated cells, a 14 day EB formation period, and further differentiation of plated EBs.
Figure 8:
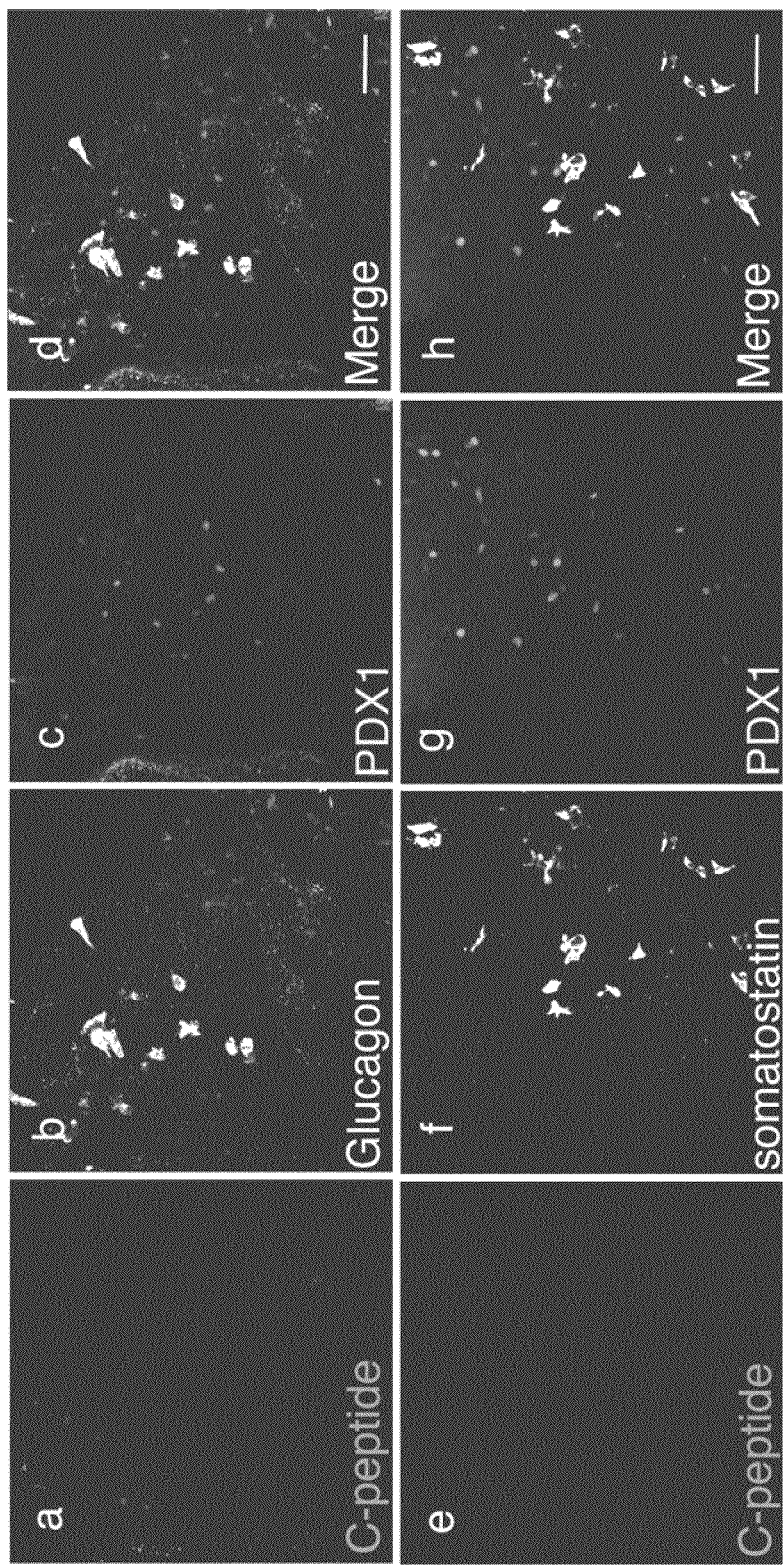
FIG. 8, comprising FIGS. 8 (*a-h*), are photomicrographs showing that glucagon-positive and somatostatin-positive cells are present at EB14+28 in cultures previously treated with BMP4.
Figure 9:
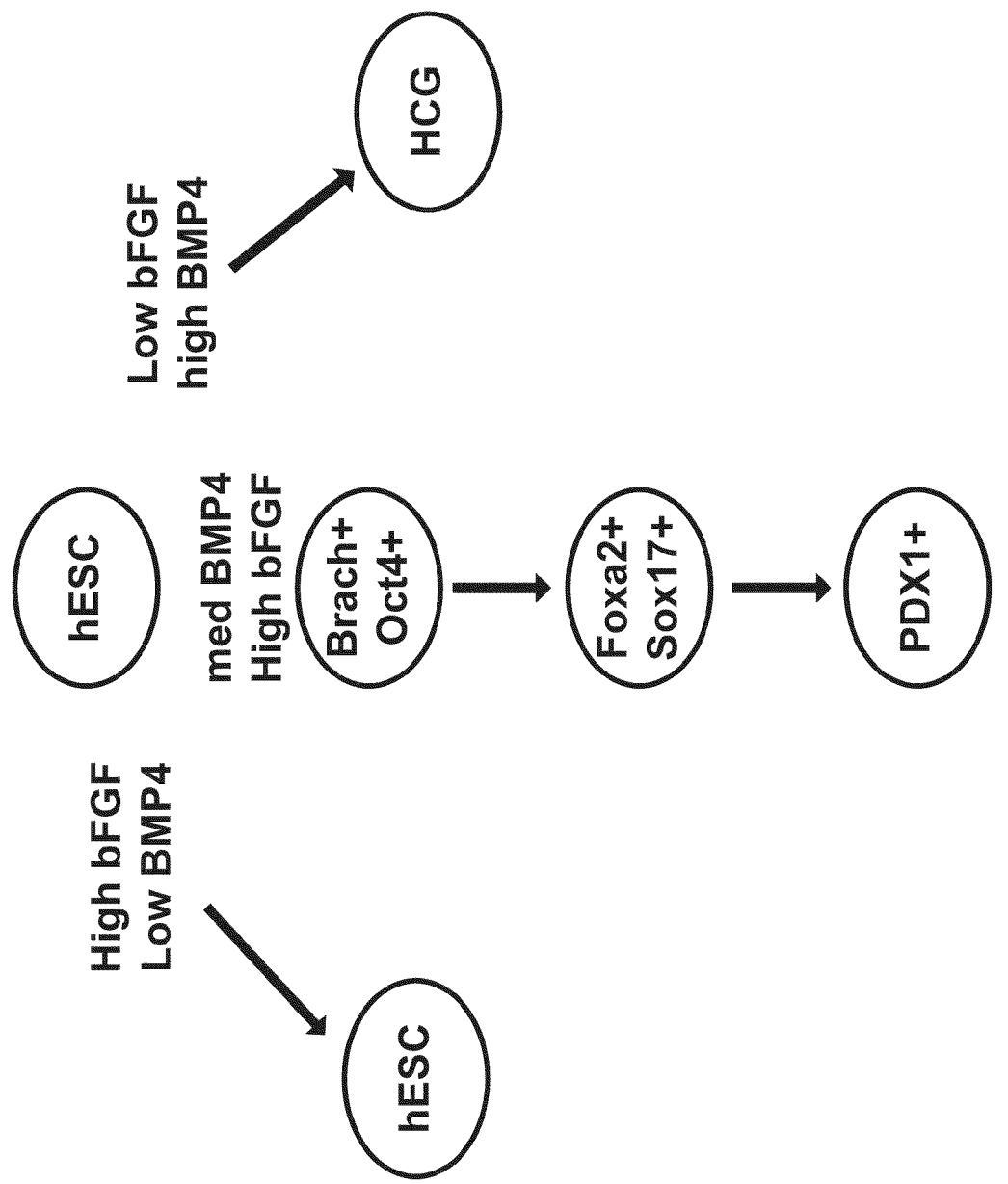
FIG. 9 is a diagram depicting how different concentrations of growth factors (BMP4 and bFGF) lead to different lineages: (left) high bFGF and low BMP4 (or with Noggin to inhibit endogenous sources of BMPs) maintain hESCs in an undifferentiated state; (center) high bFGF and medium BMP4 leads to differentiation into endoderm and pancreatic lineage cells; and (right) low bFGF and high BMP4 leads to trophoectoderm/trophoblast cells.

Consistent with gene expression results, immunostaining data show that BMP4-treated cultures contained large clusters of PDX1+ cells after plating. In contrast to PDX1+ cells found in EBs, most of the cells no longer co-stained with Ki67 (FIG. 7d-f), suggesting that the cells had begun terminal differentiation. Cells co-staining for either PDX1 and insulin, or PDX1, insulin and C-peptide appeared within the large clusters of PDX1+ cells. By 14 days after EB plating, 5 of 17 (29%) EBs showed insulin+ cells which increased over time such that by 28 days after plating, 10 of 16 (63%) EBs contained insulin+ cells and the mean # of positive cells per EB increased. The fact that applicants observed numerous insulin/C-peptide immunostained cells, which always co-express PDX1 and are localized within PDX1+ clusters, as well as a significant increase in insulin mRNA, suggests a phenotypic pattern characteristic of bona fide β cells. Glucagon and somatostatin staining was also observed in BMP4-treated cultures (FIG. 8). Glucagon+ and somatostatin+ cells did not co-stain for C-peptide as would be expected for adult endocrine cell types. Cells staining for either PDX1 or islet hormones were not observed in control group cells.

Example 8

Figure 10:
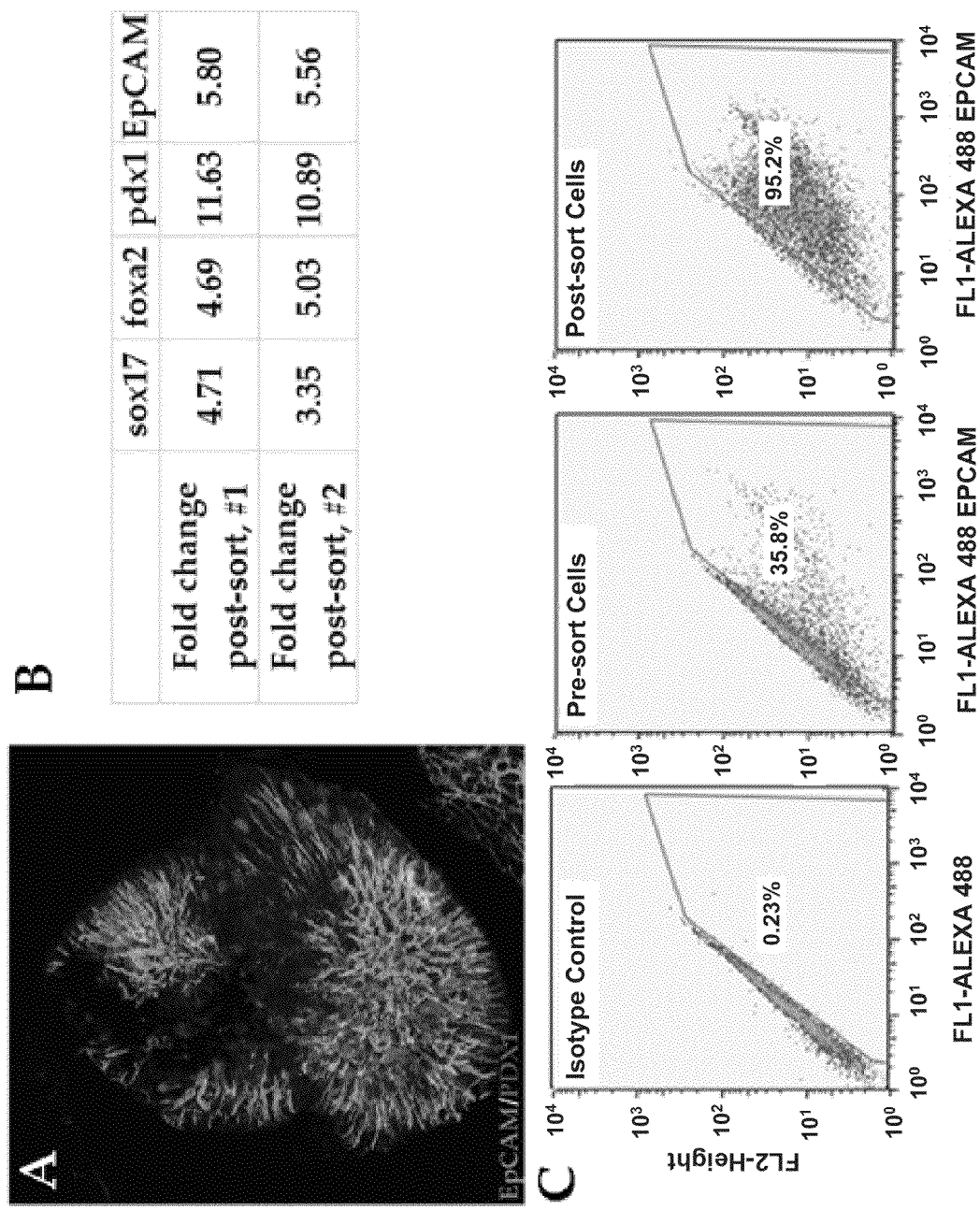
FIG. 10, comprising FIGS. 10 (*a-c*), shows that MACS-sorting for EpCAM+ cells results in enrichment of cultures for EpCAM and endoderm and pancreas-associated transcripts. (A) Differentiated hESCs co-express EpCAM (green) and PDX1 (red). Nearly all PDX1+ cells co-express EpCAM; some EpCAM+ cells that do not co-express PDX1 are also seen. (B) Fold change values from QPCR analysis of differentiated EpCAM-sorted cells compared with unsorted cells from two independent experiments. (C) FACS analysis of EpCAM expression following differentiation of hESCs by the BMP4/bFGF protocol. Cells were analyzed pre and post-MACS-sorting for EpCAM. The percent of EpCAM+ cells increases from ~35% to ~95% following MACS-sorting for EpCAM.

EpCAM Based MACS Sorting Further Enriched Cultures for Endoderm and Pancreas Committed Cells The applicant detected that when BMP4/bFGF treated cultures are stained for EpCAM and PDX1, numerous cell clusters are seen containing cells co-expressing both markers (FIG. 10a). This detection provided an opportunity to preferentially select PDX1+ cells based on EpCAM expression and MACS sorting. To test this hypothesis, cells differentiated according to the BMP4/bFGF treatment protocol are labeled with an anti-EpCAM antibody followed by labeling with an appropriate secondary antibody and sorted. After EpCAM+ sorting of differentiated hESC progeny, transcript levels of sox17 and foxa2 are increased, as are levels of pdx1 and EpCAM (FIG. 10b). In this respect, MACS sorting for EpCAM can be used to enrich or purify differentiated ESC cultures to eliminate non-endodermal cells that arise as the result of non-selective culture conditions. Sorting for EpCAM results in a population in which ~95% of the cells are EpCAM+ (FIG. 7c). Applicants hypothesize that combining two or more sorts (selecting for EpCAM and removing SSEA3 or 4+ cells) will further enrich the cultures for endoderm/pancreatic progenitor cells and simultaneously remove undifferentiated, teratoma-forming cells, from the cultures.

In summary, the methods of the invention are able to facilitate reproducible differentiation of hESCs to cells highly reminiscent of beta cells or beta-like cells. The differentiated cells are a promising source of pancreatic beta cells, which can be used to treat diabetic patients. However, little is known about cellular and molecular events regulating pancreatic differentiation in humans. As such, described herein are several components of the direct differentiation process that results in reliable and robust induction of PDX1-positive cells and generates cell clusters co-expressing PDX1 and insulin/C-peptide. The entire differentiation process is carried out in vitro in serum-free media. It was found that mesendoderm, marked by early brachyury expression, is induced when hESCs are treated with 50 ng/ml BMP4 and 100 ng/ml bFGF, and that endoderm and early proliferative pancreatic lineage cells are specified in EBs made from these cultures. Further differentiation occurs after cells are transferred to serum-free media containing insulin, transferrin, selenium, FGF7, nicotinamide and exendin-4. The in vitro-generated pancreatic cells express PDX1 and C-peptide, characteristic of β cells. These inventive findings move the field a step closer to the production of pancreatic β cell populations suitable for therapeutic purposes and facilitate the use of human pluripotent stem cells as an in vitro model of pancreas development.

The isolated populations of endodermal or pancreatic progenitor populations could enhance adult therapy. For example, these progenitor cells can be co-transplanted with human adult islets or hepatocytes. These progenitor populations may also be transplanted by themselves, without first going through the terminal differentiation step. In this therapeutic approach, it is expected that the progenitor cells will differentiate in the patient to the functional cells or tissues of interest. Regeneration of entire tissues is also envisioned starting from such endodermal or pancreatic progenitor cells.

The disclosure of every patent, patent application, and publication cited herein is hereby incorporated herein by reference in its entirety.

It is understood that certain adaptations of the invention described in this disclosure are a matter of routine optimization for those skilled in the art, and can be implemented without departing from the spirit of the invention, or the scope of the appended claims.

We claim:

1. A method of culturing human pluripotent stem cells to produce cells of the pancreatic lineage, the method comprising the steps of
   (a) culturing the stem cells under conditions that induce differentiation in the direction of mesendoderm, wherein the process of stem cell differentiation is initiated by adding an effective amount of a bone morphogenetic protein ranging from 10 ng/ml to 50 ng/ml within the first four days of initiating the stem cell culture;
   (b) culturing the cells from step (a) under conditions favoring the formation of intact embryoid bodies (EBs), wherein the EBs are surrounded by a layer of visceral yolk sac; and
   (c) culturing the cells from the EBs of step (b) under conditions favoring terminal differentiation of the cells to the pancreatic lineage.

2. The method of claim 1 wherein the culture conditions in step (c) include culturing the EB cells in a serum-free medium containing insulin, transferrin, selenium, FGF7, nicotinamide, and exendin-4.

3. The method of claim 1 wherein the bone morphogenetic protein is BMP4.

4. The method of claim 3 wherein an effective amount of BMP4 is about 50 ng/ml.

5. The method of claim 4 wherein the stem cells of step (a) are also cultured in the presence of an effective amount of a fibroblast growth factor to induce differentiation in the direction of mesendoderm.

6. The method of claim 5 wherein the effective amount of fibroblast growth factor ranges from about 10 ng/ml to about 200 ng/ml.

7. The method of claim 6 wherein the fibroblast growth factor is bFGF.

8. The method of claim 7 wherein the effective amount of bFGF is about 100 ng/ml.

9. The method of claim 1 further comprising the step of (d) selecting the cells of step (c) that positively express the epithelial cell adhesion marker (EpCAM) to retain cells of the pancreatic lineage that exhibit a reduction in tumorigenicity.

10. The method of claim 9 wherein the selecting is performed by magnetic activated cell sorting.

11. The method of claim 1 wherein the mesendoderm cells co-express Oct4 and Brachyury (T).

12. The method of claim 1 wherein the EBs include definitive endoderm cells with duct-like structures containing Foxa2+, Sox17+ and PDX1+ cells.

13. The method of claim 1 wherein the terminally differentiated cells co-express PDX1 in combination with insulin and C-peptide.

14. A method of sequentially enriching a culture derived from human pluripotent stem cells for cells of endoderm and pancreatic lineages, the method comprising the steps of
   (a) culturing the stem cells under conditions that induce differentiation in the direction of mesendoderm, wherein the process of stem cell differentiation is initiated by adding an effective amount of a bone morphogenetic protein ranging from 10 ng/ml to 100 ng/ml and fibroblast growth factor ranging from 100 ng/ml to 200 ng/ml within the first four days of initiating the stem cell culture;
   (b) culturing the cells from step (a) under conditions favoring the formation of intact embryoid bodies (EBs), wherein the EBs are surrounded by a layer of visceral yolk sac; and
   (c) culturing the cells from the EBs of step (b) under conditions favoring terminal differentiation of the cells to the pancreatic lineage.

15. The method of claim 14 wherein the culture conditions in step (c) include culturing the EB cells in a serum-free medium containing insulin, transferrin, selenium, FGF7, nicotinamide, and exendin-4.

16. The method of claim 14 further comprising the step of (d) selecting the cells of step (c) that positively express the epithelial cell adhesion molecule (EpCAM) to retain cells of the pancreatic lineage that exhibit a reduction in tumorigenicity.

17. The method of claim 16 wherein the selecting is performed by magnetic activated cell sorting.

18. A method of culturing human pluripotent stem cells to prepare a cell population of the pancreatic lineage, which does not have tumorigenic capability, the method comprising the steps of:
   (a) culturing the stem cells under conditions that induce differentiation in the direction of mesendoderm, wherein the process of stem cell differentiation is initiated by adding an effective amount of a bone morphogenetic protein ranging from 10 ng/ml to 50 ng/ml within the first four days of initiating the stem cell culture;
   (b) culturing the cells from step (a) under conditions favoring the formation of intact embryoid bodies (EBs), wherein the EBs are surrounded by a layer of visceral yolk sac;
   (c) culturing the cells from the EBs of step (b) under conditions favoring terminal differentiation of the cells to the pancreatic lineage; and
   (d) selecting for expression of a cell surface marker indicative of a commitment to a particular differentiated lineage, wherein the marker is EpCAM, the resulting cell culture not forming teratomas when injected in immunocompromised mice.

19. The method of claim 18 wherein in step (a) the mesendoderm cells are characterized by the co-expression of Oct4 and Brachyury (T) in individual cells.

20. The method of claim 18 wherein in step (b), the EBs include definitive endoderm cells with duct-like structures containing Foxa2+, Sox17+ and PDX1+ cells.

21. The method of claim 18 wherein in step (c), the terminally differentiated cells co-express PDX1 in combination with insulin and C-peptide.

22. The method of claim 18 wherein in step (d), the differentiated cells express EpCAM and do not form teratomas when injected in immunocompromized mice.

23. The method of claim 13 wherein an effective amount of a bone morphogenetic protein ranges from 10 ng/ml to 50 ng/ml and an effective amount of a fibroblast growth factor is 100 ng/ml.

* * * * *

```
                              SEQUENCE LISTING

<160> NUMBER OF SEQ ID NOS: 24

<210> SEQ ID NO 1
<211> LENGTH: 25
<212> TYPE: DNA
<213> ORGANISM: Artificial
<220> FEATURE:
<223> OTHER INFORMATION: Synthetic polynucleotide

<400> SEQUENCE: 1
ggatgaagtc taccaaagct cacgc                                               25

<210> SEQ ID NO 2
<211> LENGTH: 25
<212> TYPE: DNA
<213> ORGANISM: Artificial
<220> FEATURE:
<223> OTHER INFORMATION: Synthetic polynucleotide

<400> SEQUENCE: 2
ccagatcttg atgtgtctct cggtc                                               25

<210> SEQ ID NO 3
<211> LENGTH: 24
<212> TYPE: DNA
<213> ORGANISM: Artificial
<220> FEATURE:
<223> OTHER INFORMATION: Synthetic polynucleotide

<400> SEQUENCE: 3
ggggttctat ttgggaaggt attc                                                24

<210> SEQ ID NO 4
<211> LENGTH: 23
<212> TYPE: DNA
<213> ORGANISM: Artificial
<220> FEATURE:
<223> OTHER INFORMATION: Synthetic polynucleotide

<400> SEQUENCE: 4
attctccagg ttgcctctac atc                                                 23

<210> SEQ ID NO 5
<211> LENGTH: 20
<212> TYPE: DNA
<213> ORGANISM: Artificial
<220> FEATURE:
```

<223> OTHER INFORMATION: Synthetic polynucleotide

<400> SEQUENCE: 5
gggagcggtg aagatggaag                                            20

<210> SEQ ID NO 6
<211> LENGTH: 20
<212> TYPE: DNA
<213> ORGANISM: Artificial
<220> FEATURE:
<223> OTHER INFORMATION: Synthetic polynucleotide

<400> SEQUENCE: 6
tcaggctggg actcaagtgc                                            20

<210> SEQ ID NO 7
<211> LENGTH: 22
<212> TYPE: DNA
<213> ORGANISM: Artificial
<220> FEATURE:
<223> OTHER INFORMATION: Synthetic polynucleotide

<400> SEQUENCE: 7
aagaacggca ggaggatgtt tc                                         22

<210> SEQ ID NO 8
<211> LENGTH: 24
<212> TYPE: DNA
<213> ORGANISM: Artificial
<220> FEATURE:
<223> OTHER INFORMATION: Synthetic polynucleotide

<400> SEQUENCE: 8
cccaactctc actatgtgga ttcg                                       24

<210> SEQ ID NO 9
<211> LENGTH: 20
<212> TYPE: DNA
<213> ORGANISM: Artificial
<220> FEATURE:
<223> OTHER INFORMATION: Synthetic polynucleotide

<400> SEQUENCE: 9
gggatacgcc agtgacgacc                                            20

<210> SEQ ID NO 10
<211> LENGTH: 20
<212> TYPE: DNA
<213> ORGANISM: Artificial
<220> FEATURE:
<223> OTHER INFORMATION: Synthetic polynucleotide

<400> SEQUENCE: 10
gctctgcctc ctccacgaag                                            20

<210> SEQ ID NO 11
<211> LENGTH: 23
<212> TYPE: DNA
<213> ORGANISM: Artificial
<220> FEATURE:
<223> OTHER INFORMATION: Synthetic polynucleotide

<400> SEQUENCE: 11
gtagaaagga tgacgcctca acc                                        23

<210> SEQ ID NO 12

```
<211> LENGTH: 20
<212> TYPE: DNA
<213> ORGANISM: Artificial
<220> FEATURE:
<223> OTHER INFORMATION: Synthetic polynucleotide

<400> SEQUENCE: 12
gctgcttgct cagtgccaac                                               20

<210> SEQ ID NO 13
<211> LENGTH: 21
<212> TYPE: DNA
<213> ORGANISM: Artificial
<220> FEATURE:
<223> OTHER INFORMATION: Synthetic polynucleotide

<400> SEQUENCE: 13
acacgagacc cactttttcc g                                             21

<210> SEQ ID NO 14
<211> LENGTH: 23
<212> TYPE: DNA
<213> ORGANISM: Artificial
<220> FEATURE:
<223> OTHER INFORMATION: Synthetic polynucleotide

<400> SEQUENCE: 14
tgctggactt gtgcttcttc aac                                           23

<210> SEQ ID NO 15
<211> LENGTH: 22
<212> TYPE: DNA
<213> ORGANISM: Artificial
<220> FEATURE:
<223> OTHER INFORMATION: Synthetic polynucleotide

<400> SEQUENCE: 15
ttctacgaca gcagcgacaa cc                                            22

<210> SEQ ID NO 16
<211> LENGTH: 22
<212> TYPE: DNA
<213> ORGANISM: Artificial
<220> FEATURE:
<223> OTHER INFORMATION: Synthetic polynucleotide

<400> SEQUENCE: 16
cgtcacctcc ataccttttct cg                                           22

<210> SEQ ID NO 17
<211> LENGTH: 24
<212> TYPE: DNA
<213> ORGANISM: Artificial
<220> FEATURE:
<223> OTHER INFORMATION: Synthetic polynucleotide

<400> SEQUENCE: 17
atgctctggt ccctgtctgt atcc                                          24

<210> SEQ ID NO 18
<211> LENGTH: 24
<212> TYPE: DNA
<213> ORGANISM: Artificial
<220> FEATURE:
<223> OTHER INFORMATION: Synthetic polynucleotide

<400> SEQUENCE: 18
```

```
tgactaataa gaatgcccgt gacg                                              24

<210> SEQ ID NO 19
<211> LENGTH: 20
<212> TYPE: DNA
<213> ORGANISM: Artificial
<220> FEATURE:
<223> OTHER INFORMATION: Synthetic polynucleotide

<400> SEQUENCE: 19
cagcctttgt gaaccaacac                                                   20

<210> SEQ ID NO 20
<211> LENGTH: 21
<212> TYPE: DNA
<213> ORGANISM: Artificial
<220> FEATURE:
<223> OTHER INFORMATION: Synthetic polynucleotide

<400> SEQUENCE: 20
gctttattcc atctctctcg g                                                 21

<210> SEQ ID NO 21
<211> LENGTH: 21
<212> TYPE: DNA
<213> ORGANISM: Artificial
<220> FEATURE:
<223> OTHER INFORMATION: Synthetic polynucleotide

<400> SEQUENCE: 21
tcagatgaac gaggacaagc g                                                 21

<210> SEQ ID NO 22
<211> LENGTH: 21
<212> TYPE: DNA
<213> ORGANISM: Artificial
<220> FEATURE:
<223> OTHER INFORMATION: Synthetic polynucleotide

<400> SEQUENCE: 22
cctggcggca agattatcaa g                                                 21

<210> SEQ ID NO 23
<211> LENGTH: 20
<212> TYPE: DNA
<213> ORGANISM: Artificial
<220> FEATURE:
<223> OTHER INFORMATION: Synthetic polynucleotide

<400> SEQUENCE: 23
cggatttggt cgtattgggc                                                   20

<210> SEQ ID NO 24
<211> LENGTH: 22
<212> TYPE: DNA
<213> ORGANISM: Artificial
<220> FEATURE:
<223> OTHER INFORMATION: Synthetic polynucleotide

<400> SEQUENCE: 24
cagggatgat gttctggaga gc                                                22
```